US008894995B2

(12) United States Patent
Epshtein

(10) Patent No.: US 8,894,995 B2
(45) Date of Patent: *Nov. 25, 2014

(54) METHOD OF TREATING A DISORDER OR CONDITION OF VIRAL ETIOLOGY

(76) Inventor: Oleg Iliich Epshtein, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 12/765,385

(22) Filed: Apr. 22, 2010

(65) Prior Publication Data

US 2010/0203059 A1    Aug. 12, 2010

Related U.S. Application Data

(60) Continuation of application No. 11/656,216, filed on Jan. 22, 2007, now abandoned, which is a division of application No. 10/311,666, filed as application No. PCT/RU01/00239 on Jun. 19, 2001, now abandoned.

(30) Foreign Application Priority Data

Jun. 20, 2000 (RU) ................................ 2000115594

(51) Int. Cl.
*A61K 39/395* (2006.01)
*C07K 16/24* (2006.01)
*C07K 16/00* (2006.01)
*C07K 16/44* (2006.01)
*C07K 16/26* (2006.01)
*A61K 39/00* (2006.01)

(52) U.S. Cl.
CPC ..... *A61K 39/39583* (2013.01); *A61K 2039/505* (2013.01); *A61K 2039/545* (2013.01); *C07K 16/00* (2013.01); *C07K 16/44* (2013.01); *C07K 16/26* (2013.01); *C07K 2316/96* (2013.01); *C07K 16/24* (2013.01)
USPC ................... 424/130.1; 424/141.1; 530/387.1; 530/388.1

(58) Field of Classification Search
CPC ............. C07K 16/249; A61K 41/0004; A61K 39/3955
See application file for complete search history.

(56) References Cited

U.S. PATENT DOCUMENTS

| | | | |
|---|---|---|---|
| 3,032,584 A | 5/1962 | Bergel et al. | |
| 3,134,718 A | 5/1964 | Nobile | |
| 3,901,967 A | 8/1975 | Cohen et al. | |
| 4,292,324 A | 9/1981 | Jonsson et al. | |
| 4,839,341 A | 6/1989 | Massey et al. | |
| 4,963,367 A | 10/1990 | Ecanow | |
| 4,987,127 A | 1/1991 | Sirany | |
| 5,629,286 A | 5/1997 | Brewitt | |
| 5,683,712 A | 11/1997 | Cavazza | |
| 5,698,195 A | 12/1997 | Le et al. | |
| 5,741,488 A | 4/1998 | Feldman | |
| 5,846,514 A | 12/1998 | Foster et al. | |
| 5,879,677 A | 3/1999 | Del Zoppo | |
| 5,895,783 A | 4/1999 | Garfield et al. | |
| 6,136,309 A | 10/2000 | Novick et al. | |
| 6,143,722 A | 11/2000 | Melin et al. | |
| 6,150,500 A | 11/2000 | Salerno | |
| 6,750,197 B1 | 6/2004 | Salerno | |
| 7,572,441 B2 * | 8/2009 | Epshtein et al. | 424/130.1 |
| 7,582,294 B2 * | 9/2009 | Epshtein et al. | 424/130.1 |
| 7,700,096 B2 * | 4/2010 | Epshtein et al. | 424/130.1 |
| 7,815,904 B2 | 10/2010 | Epshtein et al. | |
| 7,923,009 B2 | 4/2011 | Epshtein et al. | |
| 8,168,182 B2 | 5/2012 | Epshtein | |
| 8,178,498 B1 * | 5/2012 | Ephstein | 514/24 |
| 8,524,229 B2 | 9/2013 | Epshtein et al. | |
| 8,617,555 B2 | 12/2013 | Epshtein | |
| 8,637,030 B2 | 1/2014 | Epshtein | |
| 8,637,034 B2 | 1/2014 | Epshtein | |
| 2002/0001588 A1 | 1/2002 | Sinha | |
| 2003/0099636 A1 | 5/2003 | Epstein et al. | |
| 2006/0165697 A1 | 7/2006 | Epstein et al. | |
| 2007/0123518 A1 | 5/2007 | Epshtein | |
| 2007/0141058 A1 | 6/2007 | Iliich et al. | |
| 2008/0025985 A1 | 1/2008 | Iliich et al. | |
| 2008/0050360 A1 | 2/2008 | Iliich et al. | |
| 2008/0131440 A1 | 6/2008 | Epshtein et al. | |
| 2009/0148521 A1 | 6/2009 | Epstehin | |
| 2010/0166762 A1 | 7/2010 | Epshtein | |
| 2010/0203059 A1 | 8/2010 | Epshtein | |
| 2010/0221258 A1 | 9/2010 | Epshtein | |
| 2010/0239569 A1 | 9/2010 | Epshtein | |
| 2011/0008452 A1 | 1/2011 | Epshtein et al. | |
| 2011/0086037 A1 | 4/2011 | Iliich | |

(Continued)

FOREIGN PATENT DOCUMENTS

EP    0687466 A1    12/1995
RU    2007989 C1    2/1994

(Continued)

OTHER PUBLICATIONS

Fechner et al., Molecules 2011, 16: 8475-8503.*
Pillemer et al., J. Rheumatol. (2003) 30: 41-43.*
Declaration filed in U.S. Appl. No. 10/522,653 on Jan. 9, 2008.*
Office Action of May 4, 2009 in U.S. Appl. No. 10/522,653.*
Declaration filed in U.S. Appl. No. 10/522,652 on Dec. 10, 2008.*
Decision by BPAI rendered on Nov. 18, 2011 in U.S. Appl. No. 09/117,838.*
Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.
Beregovoy et al., On influence of various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.

(Continued)

*Primary Examiner* — Ilia Ouspenski
(74) *Attorney, Agent, or Firm* — Pergament Gilman & Cepeda LLP

(57) ABSTRACT

A method of treating a disorder or condition of viral etiology by administration of an activated form of antibodies to an antigen, wherein said activated form is obtained by repeated consecutive dilution combined with external impact, and the antigen is a substance or a pharmaceutical agent exerting influence upon the mechanisms of formation of this particular pathological syndrome.

3 Claims, No Drawings

(56) References Cited

U.S. PATENT DOCUMENTS

| | | | |
|---|---|---|---|
| 2012/0045445 | A1* | 2/2012 | Epshtein .................... 424/145.1 |
| 2012/0225074 | A1 | 9/2012 | Epshtein et al. |
| 2012/0251584 | A1 | 10/2012 | Epshtein et al. |
| 2012/0258146 | A1 | 10/2012 | Epshtein |
| 2012/0263725 | A1 | 10/2012 | Epshtein et al. |
| 2012/0263726 | A1 | 10/2012 | Epshtein et al. |
| 2012/0294899 | A1 | 11/2012 | Epshtein et al. |
| 2012/0321672 | A1 | 12/2012 | Epshtein |
| 2013/0017202 | A1 | 1/2013 | Epshtein et al. |
| 2013/0045237 | A1 | 2/2013 | Epshtein et al. |
| 2013/0058981 | A1 | 3/2013 | Epshtein |
| 2013/0058982 | A1 | 3/2013 | Epshtein |
| 2013/0064860 | A1 | 3/2013 | Epshtein |
| 2013/0171161 | A1 | 7/2013 | Epshtein et al. |
| 2013/0189707 | A1 | 7/2013 | Sergeeva et al. |
| 2013/0224219 | A1 | 8/2013 | Epshtein et al. |
| 2013/0302312 | A1 | 11/2013 | Epshtein et al. |
| 2013/0315964 | A1 | 11/2013 | Epshtein et al. |
| 2013/0336985 | A1 | 12/2013 | Epshtein et al. |
| 2014/0010819 | A1 | 1/2014 | Epshtein et al. |
| 2014/0056923 | A9 | 2/2014 | Epshtein et al. |
| 2014/0112934 | A1 | 4/2014 | Epshtein |

FOREIGN PATENT DOCUMENTS

| | | | |
|---|---|---|---|
| RU | 2033784 | C1 | 4/1995 |
| RU | 2099052 | C1 | 12/1997 |
| RU | 2104032 | C1 | 2/1998 |
| RU | 2122858 | C1 | 12/1998 |
| RU | 2137483 | C1 | 9/1999 |
| RU | 2144370 | C1 | 1/2000 |
| RU | 98109384 | A | 3/2000 |
| RU | 2187334 | C2 | 8/2002 |
| RU | 2192882 | C1 | 11/2002 |
| SU | 1730144 | | 4/1992 |
| WO | 9412213 | A1 | 6/1994 |
| WO | 9422846 | A1 | 10/1994 |
| WO | 9520978 | A1 | 8/1995 |
| WO | 9728776 | A1 | 8/1997 |
| WO | 9814161 | A1 | 4/1998 |
| WO | 9814162 | A1 | 4/1998 |
| WO | 9833493 | A1 | 8/1998 |
| WO | 9835680 | A1 | 8/1998 |
| WO | 9921582 | A2 | 5/1999 |
| WO | 0105371 | A1 | 1/2001 |
| WO | 01/97842 | * | 12/2001 |
| WO | 03055518 | A1 | 7/2003 |
| WO | 03055519 | A1 | 7/2003 |
| WO | 03037372 | A1 | 8/2003 |
| WO | 03077946 | A1 | 9/2003 |
| WO | 2004012765 | A1 | 2/2004 |

OTHER PUBLICATIONS

Davenas et al., Nature, 1988, 333: 816-818.
Epshtein et al. May 1999, Bulletin of Experimental Biology and Medicine, vol. 5: 493-495.
Epshtein et al. Mar. 1999, Bulletin of Experimental Biology and Medicine, vol. 127, No. 3, pp. 286-289.
Frimel, G., ed., "Immunological Methods," Medicina Publishing House, 1987, pp. 9-33.
Gaevy, M.D. et al., "Osnovy klinicheskoi farmakologii I farmakoterapii," Moscow, Aliyans-B, 2002, pp. 42-44.
Goldacre (2007) Lancet 370: 1672-1673.
International Search Report from International Application No. PCT/RU02/00367, filed Aug. 2, 2002, mailed on Dec. 19, 2002.
International Search Report from International Application No. PCT/RU01/00239, filed Jun. 19, 2001, mailed on Sep. 20, 2001.
International Search Report from International Application No. PCT/RU02/00369, filed Aug. 2, 2002, mailed on Dec. 19, 2002.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Janeway et al. Immunobiology, 1997, 3rd edition, Garland Publishing Inc., pp. 3:1-3:11.
Jeger, J., Ed., "Clinical Immunology and Allergology" (Russian Translation), Meditsina, Moscow, 2000, pp. 358-359.
Kuznik, R.I. et al., "Cytomedines and their Role in Regulation of Physiological Functions," Uspekhi Sovremennoi Biologii, 1995, vol. 115, No. 3, pp. 353-367.
Linde et al., 1997, Lancet, vol. 350: 834-43.
Maini, R. N. et al., "Anti-Cytokine Therapy for Rheumatoid Arthritis," Annu. Rev. Med., 2000; 51:207-229.
Marsden, P.A. et al., "Molecular cloning and characterization of human endothelial nitric oxide synthase," FEBS Lett., vol. 307, No. 3, pp. 287-293, 1992.
Register of Pharmaceuticals of Russia, Encyclopedia of Pharmaceuticals (in Russian), Moscow, 2000, pp. 358-359.
Register of Pharmaceuticals of Russia, Encyclopedia of Pharmaceuticals (in Russian), Moscow, 2001, pp. 788-789.
Schwab, V., "Homeopathic Pharmaceutical Agents. A manual on description and preparation," Moscow, 1967, pp. 12-38.
Schwabe, W., "German Homeopathic pharmacopoeia (Homeopathisches Arzneibuch)," Stuttgart, Translation of the 5th Supplement (1991) to the 1978 edition.
Shang et al., 2005, Lancet, vol. 366: 726-32.
Stefani, D. V. et al., "Immunologiya i immunopatologiya detskogo vozrasta," Moscow, Meditsina, 1996, pp. 28, 29, 358-359.
Vasiliev, Yu, V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.
Vyazov, O.L., Laboratory Methods of Studies in Non-Infection Immunology (in Russian)m Moscow, Meditsina, 1968.
International Search Report, mailed Apr. 8, 1997, for corresponding International Patent Application No. PCT/RU97/00026, filed Feb. 10, 1997.
International Search Report, dated Dec. 5, 2002, for corresponding International Patent Application No. PCT/RU02/00368, filed Aug. 2, 2002.
International Search Report, dated Dec. 5, 2002, for corresponding International Patent Application No. PCT/RU02/00365, filed Aug. 2, 2002.
Office Action dated Nov. 5, 2013, in U.S. Appl. No. 13/889,406.
Sironi, et al., "Effect of Valsartan on Angiotensin II-Induced Plasminogen Activator Inhibitor-1 Biosynthesis in Arterial Smooth Muscle Cells", Hypertension, 2001, p. 961-966, American Heart Association, Dalla, TX.
Peterson, et al., "Using Hapten Design to Discover Therapeutic Monoclonal Antibodies for Treating Methamphetamine Abuse", The Journal of Pharmacology and Experimental Therapeutics, 2007, p. 30-39.
Nickeleit, et al., "The Classification and Treatment of Antibody-Mediated Renal Allograft Injury: Where Do We Stand?", Kidney International, 2007, vol. 71, p. 7-11.
White, et al., "Radioimmunotherapy of Relapsed B-Cell Lymphoma with Yttrium 90 Anti-Idiotype Monoclonal Antibodies", Blood Journal, 1996, vol. 87, p. 3640-3649.
Palace, "Clinical and Laboratory Characteristics of Secondary Progressive MS", Journal of Neurological Sciences, 2003, vol. 206, p. 131-134.
Revel et al., "Rodent Models of Insomnia: A Review of Experimental Procedures That Induce Sleep Disturbances", Neuroscience and Biobehavioral Reviews, 2009, p. 874-899, 33.
Erns, "Is Homeopathy a Clinically Valuable Approach?", Trends in Pharmacological Sciences, Nov. 2005, p. 547-548, vol. 26 No. 11.
Pillemer, et al., "Pilot Clinical Trial of Intravenous Doxycycline Versus Placebo for Rheumatoid Arthritis", The Journal of Rheumatology, 2003, p. 41-43.
Gilead Science, Inc., "Second Pivotal Phase III Study of Gilead's Darusentan for Resistant Hypertension Misses Primary Endpoints", Press Release, 2009, 1 page, gilead.com/pr__1365747.
Pavlov, et al., "Behavioral Effects of Potentiated Morphine Forms", Bulletin of Siberian Branch RAMS, 1999, No. 1 (91), p. 1-4.
Sensabaugh, et al., "Seminal Plasma Protein p30: Simplified Purification and Evidence for Identity with Prostate Specific Antigen", The Journal of Urology, 1990, vol. 144, p. 1523-1526.

(56) References Cited

OTHER PUBLICATIONS

Zapara, et al., "Potentiated Morphine Effect on the Electric Properties of Isolated Neurons", Bulletin of Siberian Branch of RAMS, 1999, No. 1 (91), p. 1-3.

Epshtein, Declaration filed on Oct. 28, 2008, for U.S. Appl. No. 10/522,652.

Epshtein, Declaration filed on Sep. 29, 2008, for U.S. Appl. No. 10/522,653.

Epshtein, et al. "Effects of Homeopathic Doses of Antibodies to S100 Antigen on Electric Characteristics of Neuronal Membranes", Bulletin of Experimental Biology and Medicine, 1999, No. 4, p. 423-424.

Frimel, G., ed., "Immunological Methods", Medicina Publishing House, 1987, pp. 9-33.

Grigoriev M. Yu. et al., "K probleme ispolzovaniya potentsirovannykh organnykh preparatov," Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.

Skurkovich, et al. Multiple Sclerosis 7:277-284, 2001 "Randomized study of antibodies to IFN-g and TNF-a in secondary progressive multiple sclerosis."

Non-Final Office Action dated Oct. 20, 2008 for corresponding U.S. Appl. No. 11/656,216.

Final Office Action dated Dec. 24, 2009 for corresponding U.S. Appl. No. 11/656,216.

\* cited by examiner

METHOD OF TREATING A DISORDER OR CONDITION OF VIRAL ETIOLOGY

This application is a Continuation of U.S. patent application Ser. No. 11/656,216 filed Jan. 22, 2007, which is a Divisional of U.S. patent application Ser. No. 10/311,666 filed Dec. 17, 2002 which claims the befit of International Application No. PCT/RU2001/000239, filed Jun. 19, 2001, all of which are hereby incorporate herein by reference in their entireties.

FIELD OF THE INVENTION

The invention relates to medicine and can be employed for treating various diseases and for producing pharmaceutical preparations possessing no side effects.

DESCRIPTION OF THE BACKGROUND ART

The use of antibodies for treating pathological syndromes is well known (SU 1331508 A, A 61 K 39/00, 1984; SU 1730144 A1, C 12 N 7/00, 1992).

Also known are pharmaceutical preparations based on antibodies (serums, immunoglobulins) applied in therapeutic doses. (See, for example, Register of Pharmaceutical Agents of Russia, Encyclopedia of Drugs, 7th edition, 2000, pp. 358-359).

However, the range of application of these preparations is for the most part limited to etiological treatment of infectious diseases, and their use may be associated with undesirable side effects.

DESCRIPTION OF THE INVENTION

The invention is aimed at enhancing the efficacy of treatment of pathological syndromes by the use of antibodies in activated forms for fundamentally new indications—to control a pathological syndrome; it is also intended for producing pharmaceutical substances without marked side effects.

For solution of the given problem, the method for treating a pathological syndrome includes administration of activated forms of ultra-low doses of antibodies to an antigen, wherein said activated forms are obtained by repeated consecutive dilution combined with external treatment, and said antigen is a substance or a pharmaceutical agent implicated in or exerting influence upon the mechanisms of formation of the pathological syndrome; said antigen can also represent a substance (or drug) that is, upon its introduction into the body, with non-medical purposes included, can act as direct cause of the pathological syndrome.

To this end it is expedient to use ultra-low doses of antibodies in activated forms prepared by homeopathic technology of potentiation (dynamization).

Activated forms of ultra-low doses of antibodies to a substance or a pharmaceutical agent can be also introduced together with this very substance or pharmaceutical agent implicated in or exerting influence upon the mechanisms of the pathological syndrome or directly causing the pathological syndrome.

Besides, the objective is also accomplished by a pharmaceutical agent containing activated forms of ultra-low doses of monoclonal, polyclonal or natural antibodies to an antigen, wherein said activated forms are produced by repeated consecutive dilution and external treatment predominantly based on homeopathic technology, and said antigen is a substance or a pharmaceutical agent exerting influence upon regulation of the impaired function.

At that, antibodies used in activated (potentiated) forms of ultra-low doses are raised against antigens of exogenous or endogenous origin, against autologous antigens, fetal antigens; anti-idiotypic antibodies are used too.

The drugs (pharmaceutical agents) obtained in accordance with the present invention constitute a novel class of pharmacological preparations, distinctive in combination of specific pharmacological activity, stable therapeutic action free from side effects, ecological purity and low prime cost.

EMBODIMENTS OF THE INVENTION

The pharmaceutical preparation can be prepared in the following way.

1. Obtaining of Antibodies.

Polyclonal antibodies specifically binding to compounds of various classes: proteins, polynucleotides, oligosaccharides, glycolipids, etc. and interacting with low-molecular substances (haptens) are obtained through active immunization of animals. For this purpose, animals are given a series of antigen injections according to a specially designed pattern, the antigen being either an individually isolated high-molecular substance, or a synthetic conjugate (for haptens). This procedure results in obtaining a monospecific antiserum with high content of antibodies apt for further processing. If necessary the antibodies present in the antiserum are purified. Fractionating by salt precipitation or ion exchange chromatography is used for this purpose.

Monoclonal antibodies of different specificity interacting both with low-molecular haptens and with epitopes of high-molecular substances are obtained by means of hybridome technology. At that, the initial stage of the process includes immunization based on the principles already developed for preparation of polyclonal antiserums. Further stages of work envisage yielding antibody-producing clones of hybrid cells, produced antibodies being of identical specificity. Their isolation is carried out with the same methods as for polyclonal antiserums.

Natural antibodies to exogenous antigens and biological regulators of various origins are isolated from human blood serum by the method of affinity chromatography. To this end, a carrier with a covalently bound antigen, either a hapten or a high-molecular compound is used as an immunosorbent. Chromatography yields antibodies with narrow specificity and affinity.

Methods of obtaining antibodies are described, for example, in Immunological Methods, under the editorship of G. Frimel, Moscow, Medicina Publishing House, 1987, p. 9-33).

Isolated antibodies to a substance or a pharmaceutical agent are consecutively repeatedly diluted and exposed to external treatment until ultra-low or low doses are obtained, for example, in accordance with homeopathic technology of potentiation (dynamization) (see V. Shvabe, Homeopathic Pharmaceutical Agents. A Manual on Description and Preparation, Moscow, 1967, p. 12-38). At that, the concentration is proportionally reduced through consecutive dilution of 1 volumetric part of the initial substance (antibodies) in 9 volumetric parts (for decimal dilutions, D) or in 99 volumetric parts (for centesimal dilutions, C) of a neutral solvent until the required dose (potency) is obtained; each dilution is followed by multiple vertical mechanical shaking; for each dilution separate vessel is preferable.

External treatment in the process of dilution can also be performed by sound generator or other mechanical or electromagnetic action.

The pharmaceutical preparation thus yielded is used for the most part in dosage forms and dilutions common for homeopathic practice, such as alcoholic or aqueous solutions or tablets (granules) obtained by saturating the excipient of the formulation with potentiated solution or by direct introduction of the latter into liquid dosage form of the preparation.

An example of obtaining a pharmaceutical preparation in form of activated polyclonal antibodies (antiserum) to morphine is given below.

1. Obtaining Morphine-Ovalbumin Conjugate.

Solution of 50 mg (0.001 mmol) ovalbumin in 5.0 ml of distilled water was mixed with 2.0 ml dimethylformamide containing 15.0 mg (0.039 mmol) of morphine 6-hemisuccinate and while the mixture was cooling the solution of 15 mg (0.055 mmol) of water-soluble carbodiimide in 3 ml of distilled water was added to it by drops. The reaction mixture was incubated for 5 hours at 4° C. The yielded conjugate was isolated by gel chromatography on Sephadex G25 column and exposed to lyophilization.

The quantity of conjugated morphine was calculated from UV-spectra of the original protein and the yielded conjugate by changes in absorption at 280 nm. According to UV-spectra, the synthesized conjugate contained 12-15 moles of hapten per mole of protein.

2. Obtaining a Monospecific Antiserum to Morphine-Ovalbumin Conjugate

Immunization of Viennese Blue rabbits weighing not more than 2 kg was performed in cycles with a 10-day interval between them. The maximal number of injections was four. The conjugate was injected into the area of particular lymph nodes of front and hind paws in the dose of 1 mg per immunization. To this end the antigen was previously diluted in 1 ml of complete Freund's adjuvant. The total volume of immunization mixture was 2 ml.

Subsequent immunizations were performed using incomplete Freund's adjuvant, adhering to the above-mentioned proportions of antigen and adjuvant. A test blood sample was drawn from marginal ear vein of the animal 10 days after immunization.

The rabbit blood serum was obtained by centrifugation at 1000 g for 10 minutes at room temperature; after that chloroform was added as a preservative its final concentration reaching 13%.

The antiserum obtained was tested for specific antibodies to morphine by means of enzyme immunoassay, the antibodies being detected with conjugate of enzyme-labeled anti-species (anti-rabbit) antibodies.

The obtained antiserum contained specific antibodies active in the dilution 1:1000-1:25000.

Further on, γ-globulin fraction was isolated from the yielded antiserum. To this end the protein was precipitated with 50% ammonium sulfate with subsequent rinsing of the precipitate with 30% saline solution, centrifugation and dialysis against phosphate buffer. The fraction thus prepared contained specific antibodies to morphine and was then used for producing the pharmaceutical preparation.

3. Obtaining the Activated Form (Ultra-Low Dose) of the Antibodies to Morphine.

Antiserum γ-globulins (0.5 ml) was placed into $E-6_1$ vessel and mixed with 4.5 ml of distilled water; the mixture was shaken 10 times yielding 5 ml of the first centesimal dilution. The first centesimal dilution (0.05 ml) was placed into $E-6_2$ vessel with 4.95 ml of distilled water; the mixture was shaken 10 times yielding 5 ml of the second centesimal dilution. The centesimal dilutions from the third to the twenty-ninth were prepared in a similar fashion. The thirtieth centesimal dilution was prepared by solving the twenty ninth one in 20% solution of ethanol. The yielded alcoholic solution was used for treatment purposes.

Examples of use of activated forms of ultra-low doses of antibodies conventionally designated as potentiated (dynamized) antibodies (by analogy with terminology used in homeopathic literature) for treatment of various pathological syndromes are given below.

EXAMPLE 1

Potentiated Antibodies to Hypnotic Medications

A. Patient I., aged 46, a high school instructor, had long been suffering from insomnia manifested by difficulties in falling asleep. The patient had a history of hepatitis (hepatitis and impaired metabolism of xenobiotics in the liver resulting from it probably accounted for the aftereffects of the preparation). For the last six months the patient had been taking 7.5 mg of IMOVAN at bedtime 2-3 times a week; in the morning he suffered from drowsiness and dizziness. The dose reduced to ½ tablet did not produce the desirable somniferous effect. The treatment with antibodies to IMOVAN C200 in tablets was started after discontinuation of IMOVAN intake. Two weeks later dizziness and morning drowsiness disappeared. The patient's sleep became normal.

B. Patient P., aged 62, complained of a sleeping disorder: awakening at 2-3 a.m. The patient had been using barbiturate derivatives as somniferous medications but abandoned these drugs because of their decreasing efficiency. The patient was recommended to take 10 drops of a 25% alcohol solution of potentiated monospecific antiserum to MIDAZOLAM (dormicum, flormidal, 8-chloro-6-(2-fluorophenyl)-1-methyl-4H-imidazo[1,5-a][1,4]benzodiazepine hydrochloride) at bedtime. Three days after the beginning of the treatment the patient stated that he was easier falling asleep; the sleep duration extended to 7. A continued intake of the preparation was recommended.

C. Patient Ch., aged 42, was admitted to hospital in the condition of moderate alcohol intoxication. Next morning the patient complained of tremor and disorders in coordination of movements. After a single dose of 15 ml of an aqueous solution of potentiated monoclonal antibodies to NITRAZEPAM (radedorm, 1,3-dihydro-7-nitro-5-phenyl-2H-1,4-benzodiazepine-2-one) C30 the patient fell asleep. This suggested a conclusion that the preparation was efficient in restoration of sleep in the process of arresting alcohol abstinence syndrome.

D. Patient R., aged 48, a-driver by profession, presented complaints of sleeping disorders due to overfatigue. An intranasal administration of 0.5 ml of a potentiated aqueous solution C20 of antibodies to ZOLPIDEM (N,N,6-trimethyl-2-(4-methylphenyl)imidazolo[1,2-a]pyridine acetamide) at bedtime was suggested for controlling his insomnia: At a new visit 5 days later the patient stated normalization of his sleep. Examination did not reveal any depression of reflexes or muscle tone. This suggested a conclusion that this preparation can be prescribed to the patients whose professional activities require precise coordination of movements.

E. Patient M., aged 54, complained of drowsiness and disorders in coordination of movements and presented a long-time history of the use of somniferous medications. After a 7-day course of treatment with potentiated solution of monoclonal antibodies to ZOPICLON (imovan) (6-(5-chloro-2-pyridinyl)-6,7-dihydro-7-oxo-5H-pyrrolo-[3,4-b]-pyrazine-5-ylic ester of 4-methyl-1-piperazine carboxylic acid) C50 in a dose of 1 tablet twice a day the enhancement of motor activity and sleep normalization were observed.

EXAMPLE 2

Potentiated Antibodies to Anesthetic Drugs

A. Patient M., aged 36, complained of nausea after the operation (appendectomy). For anesthesia THIOPENTAL SODIUM (monosodium salt of 5-ethyldihydro-5-(1-methylbutyl)-2-thiooxo-4,6-(1H,5H)-pyrimidinedione) had been used. An oral intake of 20 ml of a C30 homeopathic dilution of the antiserum to thiopental 3 times a day was prescribed, which made it possible to attenuate nausea.

B. Patient P., aged 28, complained of cramps in his lower extremities and hypertonicity of the gastrocnemius muscles. An oral intake of 15 ml of a C200 dilution of potentiated antiserum to SODIUM OXYBUTIRATE (sodium salt of 4-hydroxybenzoic acid) at bedtime was prescribed. The examination conducted 5 days later showed diminution of muscular tonicity.

C. Patient M., aged 6, was admitted to the otorhinolaryngologic unit for a postoperative check-up after tonsillectomy. An oral administration of a C30 solution of potentiated antibodies to KETAMINE [(+−2-(2-chlorophenyl)-2-(methylamino)cyclohexanone hydrochloride] made it possible to reduce the sensitivity of the child's mucosa and to perform an examination.

D. Patient A., aged 47, complained of hiccup and tachycardia after administration of ETHOMIDATE (ethyl ester of (R)-1-(1-phenylethyl)-1H-imidazole-5-carboxylic acid). A single oral dose of 50 ml of a homeopathic C30 solution of monoclonal antibodies to ethomidate was administered. Thirty minutes later hiccup disappeared and the cardiac rhythm was back to normal.

E. Patient D., aged 68, was admitted to a surgical hospital for a scheduled operation on benign prostatic hyperplasia. Three years earlier he had undergone an operation for urolithiasis under HALOTHANE (1,1,1-trifluoro-2-chloro-2-bromoethane) anesthesia. The postoperative period was complicated by liver function disorders manifested by dyspepsia, hyperbilirubinemia, and positive liver function tests. The patient presented a history of poor tolerance of other anesthetics. Therefore, slow intravenous infusion of 3 ml of potentiated antibodies to HALOTHANE dissolved in a 5% glucose solution was used for anesthetic purposes. The operation and the postoperative period showed no complications.

EXAMPLE 3

Potentiated Antibodies to Anticonvulsant Drugs

A. Patient B., aged 19, has been suffering from generalized epilepsy (grand mal seizures combined with psychomotor symptoms) since the age of 5. TEGRETOL (5-carbamoyl-5H-dibenz(b,f)azepine) chosen by the trial-and-error method had proved to be the most efficient anticonvulsant drug for the patient; she had been receiving a dose of 0.2 mg (1 tablet) 3 times a day for 2-years. The patient's mother consulted the attending doctor at to multiple bruises having appeared on the patient's body in the course of the last 10 days without any preceding mechanical trauma. Total blood test revealed a depressed white blood ($2.9 \times 10^3/\mu l$) and platelet count ($100 \times 10^3/\mu l$). The treatment with C30 potentiated monoclonal antibodies to the dibenzoazepine group forming the basis of the drug molecule was started whereas TEGRETOL was discontinued. Two weeks later the blood pattern was back to normal, no epileptic seizures were registered.

EXAMPLE 4

Potentiated Antibodies to Antiparkinsonian Drugs

A. Patient Z., aged 37, developed parkinsonian symptoms after vernal encephalitis. The patient had been taking daily 10 mg (4 tablets) of BROMOKRYPTINE (2-bromo-α-ergokryptine) with good effect but complained of excessive fatigue, headaches, and constipation. The treatment with potentiated antibodies to 2-bromo-α-ergokryptine (a C1000 dilution) in a daily dose of 1 tablet taken in the morning was started. Three weeks later the bowel function was back to normal and headaches subsided; however, complaints of excessive fatigue persisted.

B. Patient E., aged 72, was on LEVODOPA (3-hydroxy-1-tyrosine) for Parkinson's disease. He complained of nausea and vomiting. Antiemetic drugs of the phenothiazine group with smaller doses of LEVODOPA lead to the exacerbation of his main disease. The use of a C200 dilution of polyclonal potentiated antibodies to LEVODOPA in a dose of 1 tablet twice a day improved the patient's tolerance to the preparation.

EXAMPLE 5

Potentiated Antibodies to Neuroleptics

A. Patient E., aged 42, was admitted to a psycho-neurological dispensary in a condition of psychomotor agitation due to alcohol intoxication. Fifteen minutes after intravenous administration of 1 ml of a C30 aqueous solution of potentiated antiserum to HALOPERIDOL (4-[4-(4-chlorophenyl)-4-hydroxy-1-piperidinyl]-1-(4-fluorophenyl)-1-butanone decanoate) in a 5% glucose solution the agitation arrested and the patient went to sleep.

B. Patient L., aged 50, consulted her physician for disordered coordination of movements. The examination revealed inhibited reflexes in her low extremities, namely the knee-jerk and the Achilles tendon reflexes. She presented a long-time (1.5 months) history of FLUPHENAZINE (moditene) intake. The discontinued use of the preparation was combined with an intranasal administration of a C30 aqueous solution of monoclonal antibodies to fluphenazine (4-[3-[2-(trifluoromethyl)-10H-phenothiazine-10-yl]propyl]-1-piperazinylethanol) and a once-a-day slow intravenous administration of a dose of 1 ml. Four days later the patient's gait was back to normal and the muscle tone of her low extremities increased.

C. Patient R., aged 62, complained of restlessness and groundless night fears. Earlier she sought for physician's advice for insomnia and used to take radedorm for it. Oral administration at bedtime of the antiserum to AZALEPTINE (clozapine, leponex) (8-chloro-11-(4-methyl-1-piperazinyl)-5H-dibenzo[b,e][1,4]diazepine) in a form of 10 ml of a C200 homeopathic solution was prescribed. Seven days later phobias disappeared and the sleep became normal.

D. Patient Ch., aged 45, complained of tremor and disordered coordination of movements. He had a long-time history of neuroleptic drugs intake (haloperidol, aminazine) for schizophrenia. Oral administration of 5 ml of a C30 dilution of homeopathic solution of monoclonal antibodies to RISPERIDONE (3-[2-[4-(6-fluoro-1,2-benzisoxazol-3-yl)piperidino]ethyl]-6,7,8,9-tetrahydro-2-methyl-4H-pyrido[1,2-a]pyrimidin-4-one) twice a day by intramuscular injections was prescribed. Repeated examination 7 days later revealed absence of tremor and a tendency to normalization of the patient's gait. No psychotic disorders were observed.

E. Patient S., aged 29, suffered from depressive-paranoid form of schizophrenia. He had been taking neuroleptic drugs of the phenothiazine series for some years; the best clinical effect was noted with TISERCINE (2-methoxy-10-(3-dimethylamino-2-methylpropyl)-phenothiazine hydrochloride). During last 4 months the patient himself and his relatives drew their attention to the aggravation of extrapyramidal disorders and impaired bowel function (constipation). Total blood rest revealed depressed white blood count reaching the lower bound of normal ($3.8 \times 10^3/\mu l$). The use of a C1000 dilution of potentiated monoclonal antibodies to PHENOTHIAZINE in a dose of 1 tablet 3 times a day for 20 days (with discontinued tisercine intake) resulted in a marked relaxation of extrapyramidal disorders and normalization of the bowel function; the patient's white blood count increased to $4.7 \times 10^3/\mu l$. No psychotic disorders were present. The patient's sleep, appetite and mood were within normal limits.

F. Patient F., aged 19, suffered from oligophrenia in the form of idiocy; aggressive behavior. She received a maintaining dose of HALOPERIDOL (4-[4-(4-chlorophenyl)-4-hydroxy-1-piperidinyl]-1-(4-fluorophenyl)-1-butanone decanoate) (20 mg daily) and displayed marked extrapyramidal disorders. The lowering of the dose resulted in the enhancement of the patient's aggressiveness. The use of a C30 dilution of polyclonal potentiated antibodies to butyrophenone in a dose of 1 tablet twice a day improved the tolerance of HALOPERIDOL and made it possible to reduce the dose to 5 mg a day and subsequently to maintain the patient in a satisfactory condition by administering the potentiated preparation alone.

EXAMPLE 6

Potentiated Antibodies to Minor Tranquilizers

A. Patient V., aged 50, a research worker, has been receiving a daytime tranquilizer, MEZAPAM, for his obsessive-compulsive neurosis. He complained of drowsiness (probably caused by impaired detoxifying function of his liver). The use of a C30 dilution of potentiated polyclonal antibodies to the benzodiazepine nucleus made it possible to replace the tranquilizer. The patient's condition became satisfactory; no neurotic disorders were noted.

B. Patient E., aged 71, complained of restlessness and insomnia. Oral administration of a C200 preparation of potentiated polyclonal antibodies to DIAZEPAM (7-chloro-1,3-dihydro-1-methyl-5-phenyl-2H-1,4-benzodiazepine-2-one) in a dose of 1 tablet 3 times a day was prescribed. Four days later the district physician noted normalization of sleep along with fewer complaints of restlessness.

C. Patient S., aged 30, registered in a psycho-neurological dispensary, complained of the onset of restlessness, anxiety, and insomnia after the withdrawal of PHENAZEPAM. Oral intake of the homeopathic solution of antiserum to 2H-1,4-benzodiazepine twice a day was prescribed. After two days of treatment the normalization of sleep and mood were noticed. The general state of health was satisfactory and no anxiety was observed.

D. Patient I., aged 39, complained of fatigability, disorders in coordination of movements, and restlessness. Examination revealed no organic disorders of the central nervous system. After the diagnosis of neurasthenia was established a course of treatment with a C12 homeopathic solution of polyclonal anti-bodies to PHENIBUT (γ-amino-β-phenylbutyric acid hydrochloride) was suggested. After 2 days of oral intake (1 tablet twice a day) of the preparation tremor subsided and sleep became normal.

EXAMPLE 7

Potentiated Antibodies to Antidepressants

A. Patient V., aged 36, complained of the worsening of mood and sleeping disorders in form of early awakening along with difficulties in falling asleep. The patient also stated irritability and tremor without objective reason. An intranasal administration of 5 drops of a C30 homeopathic solution of antiserum to FLUOXETIN (PROZAC) (+−)-N-methyl-γ-[4-(trifluormethyl) phenoxy]benzolpropanamine) 3 times a day was recommended. Upon a new examination 5 days later the patient stated the betterment of his mood along with a tendency to normalization of sleep. The physician's recommendation was to continue the course of treatment.

B. Patient K., aged 39, complained of insomnia, tremor, restlessness, and impaired ability to work. He received a course of treatment with a C1000 dilution of potentiated polyclonal antibodies to FLUVOXAMINE ((E)-5-methoxy-1-[4-(trifluormethyl)phenyl]-1-pentanone-O-(2-aminoethyl) oxime) in an oral dose of 1 tablet 4 times a day. After 3 days of regular drug intake the normalization of sleep was observed along with the improvement of mood and control of restlessness.

C. Patient Sh., aged 56, complained of restlessness, feeling of fear, and sleep disorders. An intranasal administration of 1 ml of a 2% C30 solution of antiserum to AMITRIPTYLINE (3-(10,11-dihydro-5H-dibenz[a,d]-cyclohepten-5-ylidene)-N,N-dimethyl-1-propanamine) 3 times a day was recommended. Upon a new examination 3 days later the patient stated the normalization of sleep along with the reduction in the frequency and intensity of his fits of phobia. He was advised to continue this treatment; high efficacy of the drug in this particular case was noted.

D. A young man aged 18 had been suffering from enuresis since his childhood. AMITRIPTYLINE was found to have a good effect upon him. After three weeks of treatment the patient's relatives noticed his drowsiness; the patient himself complained of visual disorders (impaired accommodation) and bouts of arrhythmia from time to time. A C50 dilution of potentiated monoclonal anti-bodies to the tricyclic group, constituting the nucleus of tricyclic antidepressants was prescribed in a dose of 1 tablet twice a day. The symptoms of side effects disappeared whereas the curative action persisted.

E. Patient Ch., aged 32, a manager, presented a vast number of complaints among which the dominating were constant tiredness, poor sleep with no refreshing effect, reduced ability to work, depression, constipation along with joint and muscle aches. This condition had been lasting for more than half a year. A thorough clinical and laboratory examination revealed no psycho-neurological or somatic lesions that would account for such syndromes. The diagnosis of a chronic fatigue syndrome was established. A month of combined therapy including physiotherapy, vitamin therapy, and antidepressant IMIPRAMINE intake resulted in a mild positive effect. The treatment with a C200 dilution of potentiated antibodies to IMIPRAMINE in a dose of 1 tablet 3 times a day was begun. A week later a marked improvement in the patient's condition was noted; his ability to work increased and the number of complaints declined.

F. Patient K., aged 29, was admitted to a psycho-neurological hospital with an established diagnosis of manic-depressive psychosis in the phase of exacerbation. During examination the patient complained of the lack of motivations and tearfulness; the patient was not active physically. He used to take amitriptyline and diazepam for a long time. An oral intake of a C1000 solution of the antiserum to MOCLOBEMIDE (aurorix) (p-chloro-N-(2-morpholinoethyl)-benzamide) in the form of 5 ml of the aqueous solution 2 times a day was prescribed. A new examination 4 days later showed that the patient became more compliant; improved mood and enhanced liveliness were reported. A conclusion was drawn that the therapy was efficient.

G. Patient C., aged 49, suffered from depression and sociophobia; he had been receiving daily 225 mg of MOCLOBEMIDE (aurorix) (1.5 tablets in three doses). Despite his attending-physician's warnings the patient sometimes broke his diet. Twice after eating a cheese sandwich and a pizza with cheese he had episodes of hypertension, his blood pressure reaching 190/110 mm Hg. With moclobemide discontinued, a C30 dilution of potentiated polyclonal antibodies to moclobemide was administered in a dose of 1 tablet once a day. Further on, the treatment was well tolerated and depression symptoms subsided rapidly.

H. Patient S., aged 44, developed fluctuations of mood, tearfulness, and low vital activity caused by the climacteric period. Her psychiatrist estimated these symptoms as manifestations of a depressive syndrome. The use of traditional antidepressants caused somnolence and lethargy interfering with her professional duties. The prescription of a C12 dilution of potentiated antiserum to CERTRALINE purified by affinity chromatography in a dose of 1 tablet twice a day resulted in a rapid improvement of the patient's general state and stabilization of her mood.

EXAMPLE 8

Potentiated Antibodies to Antiemetic Drugs of Central Action

A. Patient Zh., aged 64, developed nausea and vomiting during the course of radio- and chemotherapy for peripheral lung cancer. The prescription of MOTILIUM controlled manifestations of dyspepsia but caused weakness, somnolence and intestinal cramps. With MOTILIUM discontinued, the administration of 1 ml of a C6 dilution of potentiated antibodies to MOTILIUM in the form of intramuscular injections twice a day resulted in the disappearance of neurotoxic and spastic reactions. The use of the preparation was continued with a positive clinical effect.

EXAMPLE 9

Potentiated Antibodies to Central-Action Muscle Relaxants

A. Patient B., aged 25, developed contractures of his lower extremities after a spinal trauma. MYDOCALM (1-piperidino-2-methyl-3-para-tolylpropanone-3 hydrochloride) in a dose of 300 mg a day was prescribed. After a favorable initial effect the patient noticed a gradual increase in the muscular tension in his lower extremities along with systemic arterial hypotension (105/60 mm Hg) after 2 months of the treatment. The prescription of a C200 dilution of potentiated anti-bodies to MYDOCALM in a dose of 1 tablet twice a day resulted in the normalization of arterial blood pressure (120/70) as well as in the reduction of muscular tension. The antibody therapy made it possible to reduce the dose of MYDOCALM by 25%.

EXAMPLE 10

Potentiated Antibodies to Choline Esterase Inhibitors

1A. Patient P., aged 20, with an established diagnosis of congenital myasthenia took UBRETIDE (3-oxy-1-methylpyridinium-hexamethylene-bis-(N-methylcarbamate) dibromide) (the maintaining dose was 1 tablet every other day). She started complaining of excessive salivation and abdominal cramps. The use of a D6 dilution of potentiated antibodies to UBRETIDE in a daily morning dose of 1 tablet improved the patient's tolerance of UBRETIDE without reducing its efficacy and later made it possible to switch to therapy with the potentiated preparation only.

EXAMPLE 11

Potentiated Antibodies to Psychostimulants and Nootropic Drugs

A. Patient M., aged 58, complained of memory disorders and insomnia. An oral intake of 20 drops of an alcohol solution of antibodies to NOOTROPIL (pyracetam) (2-oxo-1-pyrrolidinylacetamide) in a potency of C200 at bedtime was prescribed. During her second visit 7 days later the patient reported of an extended duration of sleep along with less difficulties in falling asleep. The recommendation was to continue the course of treatment.

B. Patient M., aged 43, was admitted to hospital in the state of alcohol withdrawal. The next day he started complaining of restlessness and tremor. A C30 dilution of potentiated antiserum to AMINALON (gammalon) (4-aminobutyric acid) in a dose of 1 tablet 6 times a day was prescribed. The reduction of tremor and the improvement of mood were noted. After 2 days of therapy the patient was discharged in a satisfactory condition.

C. Patient S., aged 72, complained of tachycardia and sleeping disorders; she presented a long-time (3 weeks) history of SYDNOCARB (3-α-methylphenyl)-N-phenyl-carbamoylsydnon imine) intake. The intranasal administration of 10 drops of a C15 solution of monoclonal antibodies to SYDNOCARB 3 times a day was prescribed. An examination after 5 days of treatment revealed the absence of tachycardia; the patient reported of less difficulties in falling asleep.

D. Patient V., aged 65, with an established diagnosis of asthenic syndrome as a remote consequence of a craniocerebral trauma had been taking MOLSIDOMINE (ethylester of N-carboxy-3-morpholino-sydnonimine) in a dose of 1 tablet 3 times a day (6 mg per diem) to prevent fits. She sought her physician's advice for headaches and worsening of sleep. After MOLSIDOMINE withdrawal the treatment with C30 dilution of potentiated monoclonal antibodies to the sydnonimine group in a dose of 1 tablet in the morning was started. The favorable effect of the treatment has been lasting for 6 months.

E. Patient D., aged 38, complained of fatigability, weakness, and headaches. The oral intake of 10 ml of a C40 dilution of potentiated polyclonal antibodies to CAFFEINE (1,3,7-trimethylxanthine) 3 times a day was prescribed. At his second visit to the physician 7 days later the patient pointed to easier awakening and the disappearance of headaches. He was recommended to continue the course of treatment.

F. Patient P., aged 35, a journalist by profession, presented symptoms of caffeine addiction: he had to drink up to 12-15 cups of strong coffee to keep himself active. The patient was emotionally labile, inclined to overestimating his own personality, and complained of poor sleep. He also had a pronounced tremor of his hands. The use of a C200 dilution of potentiated antibodies to CAFFEINE (1,3,7-trimethylxanthine) in a dose of 1 tablet 3 times a day resulted in the reduction of the amount of consumed coffee to 4-5 cups, the improvement of sleep, the disappearance of tremor, and better mood. Now the patient is active and manifests high working efficiency.

G. Patient R., aged 78, is on regular treatment with PYRACETAM (nootropil) (2-oxo-1-pyrrolidinylacetamide) in a daily dose of 1.6 g for Alzheimer's disease. The general effect of the treatment being favorable, the patient's relatives noticed enhancement of the patient's sexual activity manifested by his inappropriate behavior. The substitution of pyracetam by a C200 dilution of potentiated antibodies to PYRACETAM made it possible to get rid of sexual disinhibition while preserving the nootropic effect.

H. Patient G., aged 4, suffered from mental retardation due to a birth trauma. A 4-week course of everyday injections of CEREBROLYSINE (a complex of peptides isolated from pig brain) resulted in some improvement of the child's cognitive activity. During repeated courses of treatment cerebrolysin was substituted by a C50 dilution of potentiated polyclonal antibodies to it (in a dose of 1 tablet 2 times a day). The patient's memory became much better as well as her abilities to develop and maintain skills.

EXAMPLE 12

Potentiated Antibodies to Preparations Improving Cerebral Circulation

A. Patient L., aged 54, presented a history of cerebral atherosclerosis and an ischemic stroke a month ago. He was treated with HALIDOR (1-benzyl-1-(3-dimethylaminopropoxy)-cycloheptane fumarate) in tablets (100 mg twice a day). The patient complained of sleeping disorders and tachycardia (92 beats/min). The use of a C30 dilution of potentiated antibodies to HALIDOR (in a daily dose of 1 tablet within a month) improved his sleep; his heart rate went down to 76-80 beats/min.

EXAMPLE 13

Potentiated Antibodies to Analeptic Drugs

A. Patient T. aged 15, was admitted in the state of alcohol intoxication. Examination revealed hypotension (90/60 mm Hg), bradycardia, and nausea. The intranasal administration of 1 ml per hour of a C200 dilution of antiserum to CORDIAMINE (N,N-diethyl-3-pyridinecarboxamide) was prescribed. After 6 hours of the treatment nausea disappeared and the patient's blood pressure was back to normal.

EXAMPLE 14

Potentiated Antibodies to Anticonvulsant (Antiepileptic) Drugs

A. Patient D., aged 58, complained of tonic cramps in her lower extremities. The oral intake of calcium gluconate in combination with 10 ml of a D12 homeopathic solution of antibodies to DEPAKIN (SODIUM VALPROATE) (sodium 2-propylvalerate) at bedtime was recommended. The reduction of convulsive reactions was stated after 2 days of the therapy.

B. Patient E., aged 47, was admitted to the in-patient unit of the hospital because of the exacerbation of lumbosacral radiculitis. Within the framework of combined therapy he received, along with conventional anti-inflammatory therapy, a 25% intranasal alcohol solution (a C30 dilution) of monoclonal antiserum to FINLEPSIN (TEGRETOL) (5H-dibenz [b,f]azepin-5-carboxamide) in the form of 10 drops per dose. The next day the pain subsided and the excessive tension of back muscles reduced.

C. Patient T., aged 64, complained of insomnia and night cramps in his extremities. Within the framework of combined therapy he was receiving orally at bedtime 20 ml of a C30 dilution of potentiated antiserum to PHENOBARBITAL (5-ethyl-5-phenyl-2,4,6(1H, 3H, 5H)-pyrimidinetrione). At his new visit to the physician 10 days later the normalization of sleep was noted along with a reliable reduction in the frequency of convulsive reactions.

D. Patient I., aged 45, with an established diagnosis of generalized form of epilepsy had to give up taking LAMOTRIGINE (6-(2,3-dichlorophenyl)-1,2,4-triazine-3,5-diamine) because of nausea. The prescription of a C30 homeopathic solution of monoclonal antibodies to LAMOTRIGINE in the form of 10 intranasal drops 3 times a day instead of LAMOTRIGIN made it possible to eliminate nausea and proceed with the course of treatment. There have been no generalized epileptic fits in the course of 3-months' observation.

E. Patient U., aged 39, with an established diagnosis of epilepsy with rare absences was on PHENYTOINE (5,5-diphenyl-2,4-imidazolidinedione) treatment. She complained of dizziness and tremor for which reason and the use of the preparation was discontinued. Instead the oral intake of 20 ml of a D6 dilution of a potentiated antiserum to phenyloine 3 times a day was prescribed. Two days later the patient felt better and her tremor disappeared. No absences were registered within 8 weeks of observation.

F. Patient P., aged 49, complained of pain and tension in her gastrocnemius muscles. She gave a history of sciatic neuralgia. In order to reduce the patient's muscular tension the physician prescribed an oral intake of 20 ml of a C30 homeopathized solution of monoclonal antibodies to BACLOPHEN (β-(aminomethyl)-4-chlorobenzenepropanoic acid) 3 times a day in combination with anti-inflammatory therapy. At the new visit 7 days later she stated that her muscular rigidity and pain subsided.

EXAMPLE 15

Potentiated Antibodies to Antiparkinsonian Drugs

A. Patient D., aged 76, with an established diagnosis of Parkinson's syndrome was taking a course of treatment with LEVODOPA (3-hydroxy-L-tyrosine). As the treatment was not very efficient, the additional oral intake of a C15 dilution of monoclonal antibodies to LEVODOPA was prescribed in a dose of 1 tablet 3 times a day. The elimination of tremor was registered 3 days later, which made it possible to conclude that the therapy became more efficient. Three months later the patient was completely switched to therapy with antibodies. The tremor is insignificant. The general condition of the patient is satisfactory.

B. Patient K., aged 69, with an established diagnosis of Parkinson's syndrome due to atherosclerosis of cerebral vessels complained of nausea after the intake of SELEGILINE (DEPRENYL) ((R)—N,α-dimethyl-N-2-propenylbenzene ethanamine). The intranasal administration of 10 drops of a D24 dilution of homeopathic solution of antibodies to (R)—N,α-dimethyl-N-2-propenylbenzene ethanamine 3 times a day made it possible to eliminate nausea and to continue the course of treatment with antibodies as monotherapy.

EXAMPLE 16

Potentiated Antibodies to Preparations Used Predominantly for the Treatment of the State of Dependence A. Patient B., aged 41, had been taking a course of treatment in order to get rid of his habit of smoking. The intranasal administration of 20 drops of a C1000 dilution of the antiserum to NICOTINE (S)-3-(1-Methyl-2-pyrrolidinyl)pyridine) 2 times a day was prescribed. The patient stated the lessening of his attraction to smoking after 4 days of the treatment with the preparation.

B. Patient D., aged 19, was admitted to hospital on a suspicion of drug addiction. Two hours after the oral administration of 3 ml of a C50 homeopathic solution of antibodies to NALOXONE (5-α)-4,5-epoxy-3,14-dihydroxy-17-(2-propenyl)morphinan-6-one hydrochloride) the development of the withdrawal syndrome was registered, which was regarded as the naloxone-like effect. The further treatment with potentiated antibodies within the framework of combined disintoxication therapy made it possible to arrest the state of abstinence within 4 days.

C. Potentiated antibodies to DISULFIRAM (antabuse, (tetraethylthio-peroxydicarbodiamide).

Patient E., aged 56, was admitted to the in-patient unit of a hospital with low blood pressure (80/50 mm Hg), suffering from nausea. He presented a history of alcohol intake against the background of ESPERAL (DISULFIRAM) treatment. Five hours after the intranasal administration of 2 ml of a C30 solution of potentiated antibodies to DISULFIRAM the normalization of the patient's blood pressure and the control of nausea were achieved; however, vegetative disorders reappeared when the alcohol test was performed.

EXAMPLE 17

Potentiated Antibodies to Narcotic Analgesics

A. Patient Ch., aged 22, was admitted to the in-patient unit with signs of heroin withdrawal. In order to control his pain syndrome intramuscular injections of 1 ml of a C50 dilution of polyclonal antiserum to TRAMAL (trans-(+−)-2-[(dimethylamino)methyl]-1-3(-metoxyphenyl)cyclohexanol hydrochloride) were given twice in the course of the first hour as monotherapy. The arrest of the pain syndrome was virtually achieved. Conventional disintoxication therapy was prescribed.

B. Potentiated antibodies to BUTORPHANOL (MORADOL) (17-cyclobuthylmethyl) morphinan-3,14-diol).

Patient R., aged 24, was admitted to a narcological in-patient unit with an opiate withdrawal syndrome; the patient had been taking various opiates for long time (6 months). The oral intake of 30 ml of a C200 homeopathized solution of monoclonal antibodies to MORADOL 3 times a day lessened the intensity of the pain syndrome and the attraction to drugs.

C. Potentiated antibodies to PROMEDOL.

Patient S., aged 24, whose diagnosis was "heroin drug addiction, remission of a 7 months' duration" applied for medical advice complaining of pain in her right temporomandibular joint. No organic lesions were found after examination A D24 dilution of potentiated antiserum to PROMEDOL, (1,2,5-trimethyl-4-phenyl-4-piperidinol propanoate) was prescribed. After a single dose of the preparation the pain disappeared with background transitory manifestations of the so-called dry abstinence. When questioned, the patient reported the easing of her attraction to heroin that had increased 10 days earlier.

D. Potentiated antibodies to MORPHINE (5α,6α)-7,8-didehydro-4,5-epoxy-17-methylmorphinan-3,6-diol.

Patient Z., aged 29, underwent appendectomy. In order to control the postoperative pain he received a single 30 ml oral dose of a C30 solution of potentiated antiserum to MORPHINE at bedtime. The patient went to sleep. When questioned, he reported no feeling of euphoria upon the intake of the preparation.

E. Potentiated antibodies to PHENTANYL (N-Phenyl-N-[1-(2-phenylethyl)-4-piperidinyl]propanamide).

Patient T., aged 68, complained upon admittance of pain in her spine. She had a history of metastases of stomach cancer into the vertebral bodies and of a long-time intake of narcotic analgesics. A slow intravenous infusion of 2 ml of a D12 solution of potentiated antibodies to PHENTANYL twice a day was prescribed. After 4 days of the treatment the patient reported that the pain syndrome subsided.

EXAMPLE 18

Potentiated Antibodies to Anticholinesterase Drugs

A. Potentiated antibodies to PHYSOSTIGMINE ((3a5-cis)-1,2,3a,8,8a-hexahydro-1,3a,8-trimethylpyrrolo[2,3-b]indole-5-ol methylcarbamate). Patient F., aged 63, was under medical observation after a stroke. Objective findings: the muscular tension in the left arm was lowered. The intranasal administration of 0.5 ml of a C50 solution of potentiated monoclonal antibodies to PHYSOSTIGMINE 3 times a day was prescribed within the framework of combined therapy. After 3 weeks of the treatment normalization of the muscular tension and reflexes was observed.

B. Potentiated antibodies to PROSERINE (3-[[dimethylamino) carbonyl]-oxy]-N,N,N-trimethylbenzolaminium bromide).

Patient Ch., aged 60, after appendectomy suffered from the onset of intestinal paresis in the postoperative period. The oral intake of a C200 dilution of the antiserum to PROSERINE in a dose of 1 tablet 3 times a day was prescribed. After 4 days of the treatment the patient's gastrointestinal tract motility was back to normal.

EXAMPLE 19

Potentiated Antibodies to Anti-Glaucoma Drugs

19A. Patient Ya., aged 70, had had a long-time history of glaucoma. The patient had been taking ACETAZOLAMIDE (5-day courses of 250 mg every 6 hours) to good effect. The preparation's mechanism of action involves carbonic anhydrase blocking; on a prolonged use its efficacy is reduced due to compensatory mechanisms. Therefore, it was found necessary to discontinue the use of the preparation from time to time. During these interruptions of the treatment the attacks of glaucoma became more frequent but the patient did not tolerate any other anti-glaucoma drugs. The prescription of a C6 dilution of potentiated antibodies to ACETAZOLAMIDE in a dose of 1 tablet a day resulted in the restoration of the patient's sensitivity to the preparation; his intraocular pressure did not go beyond the upper bound of normal; the frequency of attacks of glaucoma was markedly reduced. ACETAZOLAMIDE intake was discontinued. The term of follow-up was 4 months.

EXAMPLE 20

Potentiated Antibodies to Drugs Used For Migraine

A. Antibodies to DIHYDROERGOTAMINE.

Patient N., aged 41, complained of cramping pain in the left part of her head. The diagnosis of migraine was established; the intranasal administration of a. C200 dilution of potentiated monoclonal antibodies to DIHYDROERGOTAMINE ($5\alpha,10\alpha$)-9,10-dihydro-12-hydroxy-2-methyl-5-(phenylmethyl)ergotamine-3,6,18-trione mesilate) 4 times a day was prescribed. At her next visit to the physician 7 days later the patient reported the lessening of both frequency and intensity of pain. It was recommended to continue the course of treatment.

B. Antibodies to SUMATRIPTANE (3-[2-(dimethylamino)ethyl-]N-methylindole-5-methanesulfonamide).

Patient K., aged 42, addressed herself to an out-patient clinic complaining of attacks of headache localized in the left part of her head and accompanied with nausea. The prescription was to take orally 1 ml of a D24 solution of potentiated monoclonal antibodies to SUMATRIPTANE at the time of the attack of headache together with conventional analgesics. At her next visit to the physician the patient reported the disappearance of nausea and the lessening of the intensity of pain.

EXAMPLE 21

Potentiated Antibodies to Local Anesthetics

A. Antibodies to LIDOCAINE ((2-diethylamino)-N-(2,6-dimethylphenyl) acetamide).

Patient R. aged 32, complained of heart palpitation. The diagnosis of ventricular tachyarrhythmia was established on examination. The recommendation was to take orally 1 tablet of a C12 dilution of potentiated antibodies to LIDOCAINE every hour during the attack. Using this drug, the patient reported normalization of the heart rhythm.

EXAMPLE 22

Potentiated Antibodies to Non-Steroid Antiinflammatory Drugs

A. Potentiated antibodies to DICLOFENAC (2-[(2,6-dichlorophenyl) amino]benzeneacetic acid).

Patient M., aged 52, complained of pain in his knees. The diagnosis of arthritis in the phase of exacerbation was established on examination. The prescription was: compresses with a C6 homeopathic solution of antibodies to DICLOFENAC. After four procedures the lessening of hyperemia and soreness of the joints was noticed.

B. Potentiated antibodies to INDOMETHACINE.

Patient D., aged 48, complained of pain in the epigastric area. He presented a long-time (1.5 month) history of the intake of INDOMETHACINE (1-(4-chlorobenzoyl)-5-methoxy-2-methyl-1H-indole-3-acetic acid). Gastroscopy revealed erosive gastritis. The homeopathized solution of an antiserum to indomethacine (a. C30 potency) in the form of 1 tablet 3 times a day was prescribed. At a new examination 7 days later the patient noted that the pain had disappeared.

C. Potentiated Antibodies to CYCLOOXYGENASE.

Patient F., aged 49, had been suffering from rheumatoid polyarthritis for 12 years. The use of NSAIDs of all groups including MOVALIS (a preparation with a relatively selective effect upon cyclooxygenase-2) was extremely problematic due to concomitant hyperacidic gastritis. With the background treatment with a D12 dilution of a potentiated form of antibodies to cyclooxygenase-1 in a oral dose of 1 tablet 2 times a day the patient tolerated MOVALIS well. The pain in his joints subsided and the joint motility regained. The endoscopic examination showed the remission of hyperacidic gastritis.

D. Potentiated Antibodies To IBUPROFEN ($\alpha$-methyl-4-(2-methylpropyl) benzeneacetic acid).

Patient L., aged 56, complained of pain and limited motility of her ankle joint. The oral intake of IBUPROFEN in combination with the intranasal administration of 0.5 ml of a C12 dilution of potentiated antibodies to $\alpha$-methyl-4-(2-methylpropyl) benzolacetic acid twice a day was prescribed. Five days later the normalization of joint motility and the absence of pain were noted. Ibuprofen was discontinued. The patient started receiving potentiated antibodies as monotherapy. No inflammatory symptoms or pain in her joints were found.

Potentiated Antibodies To ASPIRIN (2-(acetyloxy)benzoic acid).

E. Patient T., aged 48, complained of headaches. The examination revealed a temperature rise to 37.1° C. A C30 preparation of potentiated antibodies to ASPIRIN in a dose of 1 tablet 4 times a day was recommended. Twenty-four hours later her body temperature was back to normal and the headache subsided completely.

F. Patient T., aged 48, with an established diagnosis of ischemic heart disease developed instable angina attacks at minimal physical strain. ACETYLSALICYLIC ACID (325 mg once a day) was among the preparations the patient regularly took within the framework of combined therapy. The patient complained of stomach discomfort; a laboratory examination revealed the growth of the blood coagulation time from 5 to 12 minutes. The prescription was: 1 ml of a C12 dilution of potentiated antibodies to ASPIRIN in the form of intramuscular injections once a day. The stomach discomfort disappeared and the blood coagulation time shortened to 8 minutes.

G. Potentiated Antibodies to PARACETAMOL (N-(4-hydroxyphenyl) acetamide.

Patient N., aged 11, was admitted to the hospital with an acute respiratory tract infection. The examination revealed a temperature rise to 38.2° C. and rhinitis. In addition to halazolin, the patient started receiving orally 10 ml of an aqueous solution of potentiated antibodies to PARACETAMOL 4 times a day. Twelve hours later his body temperature was back to normal and rhinitis subsided.

EXAMPLE 23

Potentiated Antibodies to Pharmaceutical Agents Influencing the Function of Respiratory Organs A. Potentiated Antibodies to PHENOTEROL (1-(3,5-dioxyphenyl)-2-(para-oxy-$\alpha$-methyl-phenetylamino)-ethanol).

Patient K., aged 22, suffering from asthmatic bronchitis used PHENOTEROL (berotec) in an aerosol form as his main therapeutic agent. The patient stated the reliability and efficiency of the preparation but complained of hand tremor and heart palpitations associated with the medication. The use of a C30 dilution of potentiated antibodies to phenoterol in a dose of 1 tablet 2 times a day improved the patient's tolerance for the preparation without affecting its-efficacy. Gradually the patient was switched to the potentiated preparation as monotherapy. No asthmatic episodes were registered within 5 weeks of observation.

B. Potentiated Antibodies to ATROVENT.

Patient A., aged 26, suffered from polyvalent allergy including intolerance to soybeans and peanuts. He had been successfully receiving ATROVENT (in the form of an inhalation solution) for frequent attacks of bronchial asthma. After a single attempt to use ATROVENT in the form of an inhalation aerosol the patient developed a severe anaphylactic reaction. The latter was arrested by means of three intranasal administrations of 0.5 ml of a D24 dilution of antibodies to atrovent with 20-minutes intervals. Later on the patient started receiving 1 tablet a day of a D12 dilution of antibodies to atrovent every morning as monotherapy. He was feeling well and had no attacks of bronchial asthma in the course of three months.

C. Patient A., aged 45, had been taking THEOPHYLLINE for a long time for the attacks of bronchial asthma until he noted the loss of efficiency of the preparation. The oral intake of a C30 dilution of a potentiated solution of antibodies to THEOPHYLLINE (1,3-dimethylxanthine) in a dose of 1 tablet 2 times a day enhanced the efficacy of the therapy, which allowed the dose of theophylline to be reduced.

D. Patient D., aged 36, had been suffering from bronchial asthma since the age of 19. As his attacks occurred at night, he split his daily dose of 600 mg of THEOPECK into ⅔ in the evening and ⅓ in the morning. The patient complained of excessive irritability and the worsening of sleep. An attempt to reduce the dose of the preparation did not result in better sleep but nocturnal asthmatic fits became more frequent. Once the treatment with a C30 dilution of homeopathized antibodies to theophylline in a dose of 1 tablet 2 times a day had been started, the patient's sleep returned to normal within 3 weeks. The dose of theophylline was reduced to 300 mg, the asthmatic fits became rare.

E. Potentiated Antibodies to MENTHOL (2-isopropyl 5-methylcyclohexanol-1).

Patient Ch., aged 39, complained of cough and dryness in his throat. The recommendation was to take a tablet of potentiated antibodies to MENTHOL (a C12 dilution) at the onset of a coughing fit. At the next visit the patient reported the efficiency of the preparation for controlling the cough. It was recommended to continue the course of treatment.

Potentiated Antibodies to Adrenomimetic Drugs

F. Potentiated antibodies to NAPHTHIZINE, (NAPHAZOLINE) (4,5-dihydro-2-(1-naphthalinemethyl)-1H-imidazole). Patient V., aged 49, complained of tachycardia after administration of naphthizine for rhinitis. Naphtizine was replaced by a homeopathic solution (a C6 dilution) of monoclonal antibodies to 4,5-dihydro-2-(1-naphthalinemethyl)-1H-imidazole in a dose of 1 tablet 3 times a day. The patient reported normalization of his cardiac rhythm, which made it possible to continue taking the preparation. Twenty-four hours after the beginning of the treatment rhinorrhea virtually disappeared.

G. Potentiated antibodies to SALBUTAMOL (a1-[[(1,1-dimethylethyl) amino]methyl]-4-hydroxy-1,3-benzene-dimethanol).

Patient I., aged 54, complained of hard breathing fits. The intranasal instillations of a C50 homeopathic solution of antibodies to SALBUTAMOL in the form of 5 drops of an aqueous solution 3 times a day were prescribed. The use of the preparation made it possible to shorten the duration of hard breathing fits.

EXAMPLE 24

Potentiated Antibodies to Histamine and Antihistamine Drugs

A. Potentiated antibodies to CROMOLYN (5,5-[(2-hydroxy-1,3-propanediyl)-bis-(oxy)]-biz-[4-oxo-4H-1-benzopyrane-2-carboxylic acid).

Patient M., aged 57, had been suffering from seasonal pollinosis. The prescription of 1 ml of a C30 dilution of potentiated antibodies to CROMOLYN in the form of nasal drops 2 times a day made it possible to control the symptoms of rhinitis.

B. Potentiated antibodies to ZADITEN (KETOTIFEN) (4,9-dihydro-4-(1-methyl-4-piperidinylidene-10H-benzo[4,5]cyclohepta[1,2-b]-thiophen-10-one hydrofumarate).

Patient M., aged 29, a software programmer by profession has been suffering from pollinosis with symptoms of kerato-conjunctivitis during spring and summer. He used to control exacerbations of his condition with 1 mg of ZADITEN (1 tablet) 2 times a day. The positive therapeutic effect of ZADITEN intake was accompanied by a depressed intensity of emotional and physical reactions, somnolence and listlessness. The administration of a C30 dilution of potentiated antibodies to ZADITEN in a dose of 1 tablet 2 times a day resulted in the elimination of ZADITEN's side effects. The ZADITEN intake was discontinued; the patient continued to receive the potentiated preparation as monotherapy. No manifestations of hay fever were noted afterwards.

C. Potentiated antibodies to TAVEGYL (1-methyl-2[2-(α-methyl-para-chlorbenzhydryl-oxy)-ethyl]-pyrrolidine).

Patient Ch., aged 35, used to take TAVEGYL to good effect for chronic urticaria. The parenteral administration of TAVEGYL (in a dose of 2 ml intramuscularly) in the case of the next exacerbation accompanied by a pronounced allergic skin syndrome and a high eosinophile count (18%) in the peripheral blood resulted in a rapid clinical and laboratory improvement (eosinophile count going down to 7%); however, headache, nausea, and mouth dryness were noted. The administration of a C12 dilution of potentiated polyclonal antibodies to TAVEGYL in a dose of 1 tablet 2 times a day resulted in the elimination of the side effects of TAVEGIL use. Further on, the patient has been receiving TAVEGIL in combination with potentiated antibodies to TAVEGIL; a month later she was put on a maintaining dose of antibodies (once in three days) as monotherapy.

D. Patient S., aged 48, was admitted to the pulmonology unit for pneumonia. The patient had an anaphylactic shock in response to the intravenous injection of calcium chloride. The intramuscular injection of 1 ml of C50 dilution of potentiated antibodies to HISTAMINE made it possible to arrest the symptoms of shock within 5 minutes.

E. Potentiated Antibodies to KETOTIFEN (4,9-dihydro-4-(1-methyl-4-piperidinylidene)-10H-benzo[4,5]cyclohepta[1,2-b]thiophen-10-one hydrofumarate).

Patient D., aged 12, was hospitalized because of his complaint of heavy breathing during the season of poplar blossoming. The oral intake of 10 ml of a C24 dilution of homeopathic solution of antiserum to KETOTIFEN 3 times a day restored the patient's respiratory function to the normal level.

Potentiated antibodies to inhibitors of H1-histamine receptors.

F. Potentiated antibodies to LORATIDINE (CLARITINE) (ethyl ester of 4-(8-chloro-5,6-dihydro-11H-benzo-[5,6]cyclohepta[1,2-b]pyridin-1-ylidene-)-1-piperidine carboxylic acid).

Patient K., aged 45, complained of an itching sensation in her nasopharynx after working with paintwork materials. After the administration of a C200 dilution of potentiated monoclonal antibodies to LORATIDINE (in a dose of 1 tablet 2 times a day) itching subsided. It was concluded that the preparation had proved its efficiency.

Potentiated antibodies to TAVEGYL (CLEMASTINE) ([R—(R*,R*)]-2-[2-[1-(4-chlorophenyl)-1-phenylethoxy]ethyl]-1-methylpyrrolidine fumarate or 1-methyl-2[2-(α-methyl-para-chlorbenzhydryl-oxy)-ethyl]-pyrrolidine fumarate).

Patient P., aged 34, complained of somnolence after the intake of TAVEGIL for the itching of her elbows. The oral intake of a D6 dilution of potentiated antibodies to [R—(R*,R*)]-2-[2-[1-(4-chlorophenyl)-1-phenyl-ethoxy]ethyl]-1-methylpyrrolidine fumarate in a dose of 1 tablet 2 times a day was recommended. At her next visit to the physician the patient reported that her drowsiness had subsided and her mood improved. She was put on the potentiated preparation as monotherapy. At her visit to the physician 2 months later the patient reported that her itching had virtually disappeared.

EXAMPLE 25

Potentiated Antibodies to Medications Used for Treatment of Erosive Lesions of Gastrointestinal Tract Potentiated Antibodies to inhibitors of H2-histamine receptors.

A. Potentiated Antibodies to RANITIDINE (N-[2]-[[[5-[(Dimethylamino)methyl]-2-furanyl]methyl]thio]ethyl]-N-methyl-2-nitro-1,1-ethendiamine).

Patient N., aged 56, complained of epigastric pain. The prescription was: 1 tablet of a C12 dilution of a potentiated polyclonal antiserum to RANITIDINE (N-[2]-[[[5-(dimethylamino)methyl]-2-furanyl]-methyl]-thio]-ethyl]-N-methyl-2-nitro-1,1-ethendiamine) to be taken after meals. After 3 days of the treatment the pain disappeared.

B. Potentiated antibodies to FAMOTIDINE (3-[[[2-[(aminoiminomethyl)-amino]-4-thiazolyl]-methyl]-thio]-N-(aminosulfonyl)-propaneimidamide).

Patient G., aged 45, complained of nausea after meals. Gastroscopy revealed gastritis in an exacerbation phase. The recommendations involved diet and the oral intake of 10 ml of a C30 solution of potentiated polyclonal antibodies to FAMOTIDINE before meals. After 5 days of the treatment the patient's general condition and the gastroscopic pattern of his gastric mucosa were back to normal.

Potentiated Antibodies to Proton Pump Inhibitors

C. Potentiated antibodies to OMEPRAZOLE (5-metoxy-2-[[(4-metoxy-3,5-dimethyl-2-pyridinyl)methyl sulfonyl] 1H-benzimidazole).

Patient U., aged 33, felt a pronounced pain in the pit of the stomach from time to time. Gastroscopy revealed erosive gastritis. After the administration of a C12 homeopathic dilution of the preparation of polyclonal antibodies to OMEPRAZOLE in a dose of 1 tablet-3 times a day along with a diet the gastric mucosa was back to normal 6 days: later and both frequency and intensity of pain diminished.

25D. Patient A., aged 44, with an established diagnosis of ulcerative disease of stomach and duodenum in the phase of exacerbation had been taking OMEZ (20 mg daily, a proton pump inhibitor) for 4 weeks. Against the background of an improvement of the course of the disease the patient complained of dizziness and headache. The treatment with a D12 dilution of potentiated antibodies to OMEZ in a dose of 1 tablet 3 times a day resulted in the elimination of side effects on the part of the central nervous system and in the improvement of the patient's general condition within 3 days. Later on, the remission was maintained solely by the intake of potentiated antibodies to OMEZ.

Potentiated antibodies to M-cholinolytic drugs.

E. Potentiated antibodies to PIRENZEPINE (GASRTOZEPINE) (5,11-dihydro-11-[(4-methyl-1-piperazinyl)acetyl]-6H-pyrido[2,3-b][1,4]benzodiazepine-6-one).

Patient P., aged 57, complained of tremor and pain in the pit of his stomach after meals. Gastroscopy revealed no organic lesions of stomach mucosa. The oral intake of a D8 homeopathic solution of antiserum to GASRTOZEPINE in a dose of 1 tablet before meals was recommended. A new examination 10 days later showed an improvement of the patient's mood; no epigastric pain was noted. It was concluded that the preparation was efficient.

F. Potentiated antibodies to ATROPINE (8-methyl-8-azabicyclo[3.2.1]oct-3-yl ester of endo-(+−)-α-(hydroxymethyl)benzolacetic acid).

Patient M., aged 41, suffered of cramps in his right subcostal area 2 hours after meals rich in fat. The prescription was: a diet and the oral intake of a C200 aqueous solution of potentiated polyclonal antibodies to ATROPINE in a dose of 10 ml (after meals). The pain syndrome subsided 2 days later. It was recommended to continue the course of treatment.

G. Patient F., aged 42, suffered from sinus bradycardia; his pulse rate was 48 beats/min. He had been taking the Belladonna Extract in tablets; the positive therapeutic effect of the extract (the pulse rate increased to 64 beats/min) was accompanied by general weakness and dryness of skin and mucosae. (ATROPINE, the active principle of the extract, is the tropinic ester of d,l-tropic acid; the L isomer is active whereas the D isomer manifests low activity). The recommendation was to take alternately potentiated antibodies (a C15 dilution) to both isomers. The patient's pulse rate stabilized at 64 beats/min; no cholinolytic side effects were observed.

H. Antibodies to NO-SPA (drotaverine) ([(3,4-diethoxyphenyl)methylene]-6,7-diethoxy-1,2,3,4-tetrahydroisoquinoline).

Patient L., aged 38, complained of epigastric pain and belching. His examination revealed no organic lesions. The prescription was: the oral intake (before meals) of an aqueous solution (a C6 dilution) of monoclonal antibodies to NO-SPA (drotaverine) in a dose of 15 ml. After 2 days of the treatment the patient stated the lessening of dyspeptic manifestations.

EXAMPLE 26

Potentiated Antibodies to Antiemetic Drugs

A. Potentiated antibodies to DOMPERIDONE (MOTILIUM) (5-Chloro-1-[1-[3-(2,3-dihydro-2-oxo-1H-benzimidazol-1-yl)propyl]-4-piperidinyl]-1,3-dihydro-2H-benzimidazol-2-one).

Patient N., aged 71, had been treated with levodopa for parkinsonism and had to stop the therapy because of nausea and vomiting. The oral intake of levodopa in combination with 30 ml of a C30 dilution of an aqueous solution of potentiated monoclonal antibodies to MOTILIUM was prescribed, which made it possible to eliminate vomiting and continue antiparkinsonic therapy.

B. Patient Zh., aged 64, developed nausea and vomiting in response to radio- and chemotherapy he had been getting for peripheral lung cancer. The prescription of MOTILIUM controlled symptoms of dyspepsia but the patient developed weakness, drowsiness, and intestinal cramps. MOTILIUM was discontinued and a C6 dilution of potentiated antibodies to MOTILIUM was administered in a dose of 1 ml intramuscularly 2 times a day, which resulted in the elimination of neurotoxic and spastic reactions. The treatment was continued with a positive clinical effect.

C. Patient Yu., aged 55, suffered from chronic gastritis and esophagitis. He had been taking MOTILIUM (the active principle is DOMPERIDONE, an antagonist of dopamine receptors) for 3 months in a dose of 10 mg 15-20 minutes before meals on his own initiative under the influence of commercial advertising. He sought for medical advice because of gynecomastia he had noticed. Motilium was discontinued and a C1000 dilution of potentiated antiidiopathic antibodies to DOMPERIDONE was prescribed for 2 months in a dose of 1 tablet a day. The symptoms of gynecomastia disappeared and dyspeptic problems never resumed.

D. Potentiated antibodies to METOCLOPRAMIDE (REGLAN, CERUCAL) (4-amino-5-chloro-N-[2-(diethylamino)ethyl]-2-metoxybenzamide). Patient D., aged 38, complained of nausea and belching after meals. A course of treatment with an oral preparation containing a C30 dilution of potentiated antibodies to METOCLOPRAMIDE (REGLAN, CERUCAL) in a dose of 2 tablets before meals was prescribed. Four days later the patient reported the disappearance of nausea. A conclusion about the efficiency of the preparation was drawn.

EXAMPLE 27

Potentiated Antibodies to Antitussive Drugs

A. Potentiated antibodies to CODEINE ((5α,6α)-7,8-didehydro-4,5-epoxy-3-methoxy-17-methylmorphinan-6-ol).

Patient B., aged 47, complained of fits of dry cough. The diagnosis was: chronic bronchitis; the intranasal administration of a C200 dilution of an aqueous solution of potentiated monoclonal antibodies to CODEINE in a dose of 5 drops during a fit was recommended. Twenty-four hours after the beginning of the treatment the elimination of cough was registered.

B. Potentiated antibodies to LIBEXIN (PRENOXDIAZINE) (1-[2-[3-(2,2-diphenylethyl)-1,2,4-oxydiazol-5-yl]ethyl]piperidine).

Patient T., aged 41, had been taking LIBEXIN tablets for her cough. She complained of dryness in her mouth and throat. LIBEXIN was discontinued. The suggestion was to take orally a C50 dilution of a potentiated antiserum to 1-[2-[3-(2,2-diphenylethyl)-1,2,4-oxydiazol-5-yl]ethyl]piperidine in a dose of 1 tablet 3 times a day. The administration of the homeopathic preparation eliminated the undesired symptoms within 2 hours. The examination two days later showed a satisfactory general condition of the patient and the absence of cough.

EXAMPLE 28

Potentiated Antibodies to Various Groups of Antihypertensive Drugs

Potentiated antibodies to sympatholythics.
A. Potentiated antibodies to RESERPINE
Patient B., aged 36, had been taking a course of treatment with ADELPHAN for arterial hypertension. After 3 weeks of the treatment she started complaining of dizziness. The examination revealed that her blood pressure had dropped to 105/60 mm Hg. ADELPHAN was discontinued. The oral intake of a C12 dilution of potentiated antiserum to RESERPINE in a dose of 1 tablet 2 times a day was prescribed. Two days later her dizziness subsided and the blood pressure rose to 115/70 mm Hg.

B. Patient P., aged 72, suffered from hypertensive disease, Stage II b. She had been taking RAUNATINE (1 tablet 2 times a day) for a long time to good effect. The patient complained of dizziness and stuffiness in her nose not associated with a common cold. A C50 dilution of potentiated antibodies to RESERPINE was prescribed; this agent lessened her dizziness and completely eliminated stuffiness in her nose. Later on, she had been taking the preparation for 3 months in a dose of 1 tablet 2 times a day. Her blood pressure stabilized at a level of 140/90 mm Hg.

Potentiated antibodies to α-adrenolytic drugs.
C. Potentiated antibodies to PRAZOSIN (MINIPRESS) (1-(4-amino-6,7-dimethoxy-2-quinazolinyl)-(2-furanylcarbonyl)piperazine).

Patient Ch., aged 53, complained of headaches after the intake of PRAZOSIN for hypertensive disease. The prescription of a C30 dilution of a potentiated antiserum to (1-(4-amino-6,7-dimethoxy-2-quinazolinyl)-(2-furanylcarbonyl) piperazine) in a dose of 1 tablet together with the intake of the PRAZOSIN resulted in the lowering of the patient's blood pressure. Later on, he started the administration of the antibodies as monotherapy; the blood pressure did not rise above his optimal level of 150/90 mm Hg.

D. Patient I., aged 64, with an established diagnosis of arterial atherosclerosis (predominantly of the vessels of his lower extremities) and hypertensive disease, Stage IIb, had been taking PRAZOSIN in a dose of 8 mg a day (16 tablets). The patient complained of nausea and constant drowsiness. An attempt to reduce the dose on his own initiative resulted in a rise of the blood pressure and reappearance of the pain in his legs. The administration of a C12 dilution of potentiated antibodies to PRAZOSIN in a dose of 1 tablet 3 times a day made it possible to eliminate the undesirable manifestations and to reduce the dose of PRAZOSIN to 10 mg a day. Two months later the patient switched to the maintaining dose of 1 tablet a day of a C50 dilution of potentiated antibodies to PRAZOSIN.

E. Patient Shch., aged 69, has been receiving 1 tablet of OMNIC (400 mg after breakfast) for benign hyperplasia of the prostate. The patient developed symptoms of orthostatic hypotension. The treatment with a C30 dilution of potentiated antibodies to OMNIC in a dose of 1 tablet 3 times a day was begun. Orthostatic symptoms disappeared 2 days later whereas the therapeutic effect of the preparation was preserved: the patient felt better, the volume of the residual urine diminished and the frequency of urinations reduced.

Potentiated antibodies to CLOFELINE (2,6-dichloro-N-2-imidazolidinylidenbenzamine).

F. Patient E., aged 58, complained of drowsiness after the administration of CLOFELINE she had been taking for hypertensive disease. The recommendation was to combine the intake of CLOFELINE and a C12 solution of monoclonal antibodies to 2,6-dichloro-N2-imidazolidinylidenbenzamine in a dose of 1 tablet 3 times a day. After two days of the treatment the patient stated the improvement of her mood and an enhanced motor activity. CLOFELINE was gradually discontinued. Now the patient receives only the potentiated drug; the arterial blood is stable.

G. Patient Yu., aged 59, had a 10-years' history of essential hypertension. A regular intake of CLOFELINE in a dose of 0.6 mg a day produced a favorable effect on the course of his illness. He sought for medical advice at his district out-patient clinic because of dryness in the mouth. Several weeks of the administration of a C200 dilution of potentiated antibodies to CLOFELINE in a dose of 15 drops of an aqueous solution 4 times a day resulted in the elimination of the undesirable manifestations. The patient was switched to the potentiated preparation alone as the maintaining therapy.

Potentiated antibodies to isomers of NEBILET.

H. Patient R., aged 63, with an established diagnosis of hypertensive disease, Stage IIa, was on NEBILET treatment (the drug contains two isomers; both are biologically active but their metabolization rate varies in different people). The patient complained of nightmares, which had not been experienced before the NEBILET administration. Pharmacokinetic studies showed that the patient belonged to the group with a slow type of metabolism (high difference in the concentrations of L- and D-enantiomers in the plasma). The administration of a D24 dilution of potentiated antibodies to L-isomer in a dose of 1 tablet 3 times a day resulted in the normalization of sleep along with the conservation of a good hypotensive effect.

I. Patient P., aged 67, has been taking LABETALOL (400 mg a day) for hypertensive disease. The patient complained of heavy breathing. A C15 dilution of potentiated antibodies to RR-isomer in an oral dose of 10 ml two times a day was prescribed. After two days of treatment the patient's condition improved and functional tests showed the improvement of bronchial conduction.

Potentiated antibodies to inactive isomers of LABETALOL.

J. Patient A., aged 57, with an established diagnosis of hypertensive disease and ischemic heart disease took LABETALOL and complains of heavy breathing and dizziness. The prescription was: a mixture of a C30 dilution of potentiated antibodies to inactive isomers in a dose of 1 sachet of powder a day. The patient's condition improved and the dose of the drug was reduced from 400 mg to 50 mg a day.

K. Patient Ya., aged 61, with an established diagnosis of hypertensive disease and ischemic heart disease took APRESSIN (HYDRALAZINE) (1-hydrazinophthalazine hydrochloride) 250 mg a day in 4 doses. She complained of headaches, hot flashes, and nausea. An attempt to reduce the dose did not result in the desired effect. The recommendation was start taking a D8 dilution of potentiated monoclonal antibodies to the hydrazine group of the APRESSIN molecule; this group is capable of inhibiting the inactivation of endogenous vasodilating factors (NO in particular). After two days of treatment with this preparation in a dose of 1 tablet before meals the patient noticed the improvement of her condition. The treatment with APRESSIN was continued; its dose was reduced without any attenuation of its pronounced therapeutic effect and two months later APRESSIN was discontinued. The patient was put on monotherapy with the antibodies.

Potentiated antibodies to calcium channel blockers.

Potentiated antibodies to NORVASK (AMPLODIPINE) (3-ethyl-5-methyl ester of 2-[(2-aminoethoxy)methyl]-4-(2-chlorophenyl)-1,4-dihydro-6-methyl-l-3,5-pyridine dicarboxylic acid).

B. Patient Ch., aged 59, took NORVASK for hypertensive disease. He complained of headache after the intake of the preparation. The prescription was: the intranasal administration of 1 ml of a C1000 dilution of potentiated antiserum to 3-ethyl-5-methyl ester of 2-[(2-aminoethoxy)methyl]-4-(2-chlorophenyl)-1,4-dihydro-6-methyl-3,5-pyridine dicarboxylic acid once a day in the form of 10 drops to be taken 3 times a day. The next day his headache disappeared. The patient kept taking the two medications together. Six months later the patient was put on monotherapy with the potentiated preparation.

Potentiated antibodies to the antagonists of Angiotensin Converting Enzyme (ACE) and of angiotensin-2 receptors.

Potentiated antibodies to CAPTOPRIL ((S)-1-(3-mercapto-2-methyl-1-oxopropyl)-L-proline):

M. Patient L., aged 40, complained of periodical headaches and episodes of hypertension. The oral intake of a C50 homeopathic solution of potentiated anti-bodies to CAPTOPRYL in a dose of 5 ml 2 times a day was recommended. Within 10 days of the treatment a decrease in the frequency of headaches was noticed.

Potentiated antibodies to LOSARTAN (COZAAR) (2-butyl-4-chloro-1-[[2-(1-tetrazol-5-yl)[1,1'-biphenyl]-4-yl]methyl]-1H-imidazole-5-methanol).

N. Patient G., aged 46, complained of tremor. He had a history of LOSARTAN intake for his hypertensive disease. The recommendation was to take a D24 dilution of potentiated antibodies to 2-butyl-4-chloro-1-[[2-(1H-tetrazol-5-yl)[1,1'-biphenyl]-4-yl]methyl]-1H-imidazole-5-methanol in a dose of 1 tablet 2 times a day. After three days of the treatment the tremor disappeared. Later on, in order to keep his blood pressure stable the patient received only potentiated antibodies.

O. Patient E., aged 42, with an established diagnosis of essential arterial hypertension had been taking MOXONIDINE in a dose of 300 mg a day. The patient complains of dryness in his mouth and drowsiness. The treatment with a C30 dilution of potentiated antibodies to MOXONIDINE produced a positive effect. Later on, the patient was put on preventive treatment with antibodies to MOXONIDINE in a dose of 1 tablet a day.

P. Patient M., aged 58, with an established diagnosis of essential arterial hypertension, Stage 11b had been taking ENALAPRIL (1-[N—[S]-1-carboxy-3-phenylpropyl]-L-alanyl]-L-proline-1'-ethyl ester), an angiotensin-converting enzyme inhibitor) on her physician's advice in a dose of 20 mg once a day. She complains of cough and dyspepsia. The patient used to take medications for the treatment of the intestinal microflora disorder on her own initiative with no positive results. The bacteriological testing of her intestinal microflora yielded no pathological findings: ENALAPRIL was discontinued. The new therapy scheme included the addition of a C200 dilution of potentiated antibodies to ENALAPRIL in a dose of 1 tablet once a day. The patient's bowel function normalized and the cough ceased.

Q. Patient Z., aged 47; with an established diagnosis of hypertensive disease had been taking VALSARTAN in a dose of 80 mg a day. She complained of incessant cough and pharyngitis. Neither X-ray examination nor phthisiologist's and otolaryngologist's consultations revealed any pathology. The administration of C30 potentiated antibodies to VALSARTAN in a dose of 1 tablet 2 times a day eliminated the side effects of the preparation. After that the dose of VALSARTAN was reduced first to 40 mg a day and later to 20 mg a day with a stable hypotensive effect.

Potentiated antibodies to DILTIAZEM.

R. Patient C., aged 54, with an established diagnosis of hypertensive disease, ischemic heart disease, angina decubitus had been taking DILTIAZEM in a dose of 40 mg 4 times a day with good clinical effect. Rare attacks of angina: about once a week. After 1.5 month of treatment the patient noticed the slowing of the pulse rate (from 72 to 48-52 beats/min); the ECG indicated the extension of the P-Q interval from 0.12 to 0.20 s. The treatment with a D24 dilution of potentiated polyclonal antibodies to DILTIAZEM in a dose of 1 tablet 3 times a day was prescribed. The patient's pulse rate reached 60 beats/min, the P-Q interval shortened to 0.15 s, without angina attacks becoming more frequent. The dosage of DILTIAZEM was reduced to 20 mg 2 times a day.

Potentiated antibodies to spasmolytic drugs.

Potentiated antibodies to DIBAZOLE (2-(phenylmethyl)-1H-benzimidazole).

S. Patient Z., aged 41, complained of headache and nausea. The diagnosis of hypertensive disease was established and the oral intake of a C12 homeopathic solution of polyclonal antibodies to DIBAZOLE in a dose of 1 tablet 2 times a day was recommended. Ten days later the patient reported feeling better and not suffering from headaches.

EXAMPLE 29

Potentiated Antibodies to Substances Taking Part in Natural Regulation of the Blood Pressure A. Patient S., aged 46, had been sent to hospital within several years because of hypertension crises. Once a crisis had been arrested the patient was put on the maintaining therapy with captopril. In order to enhance the hypotensive effect a C12 dilution of potentiated antibodies to RENIN in a dose of 1 tablet 2 times a day was added to the treatment. Combined therapy made it possible for the first time in many years to lower the patient's blood pressure to 140/100 mm Hg. The patient's condition is satisfactory.

B. Patient H., aged 38, suffered from therapy-resistant essential hypertension. The closest to optimal drug for the patient was ENALAPRIL, which made it possible to stabilize the blood pressure at 160/110 mm Hg. The treatment protocol with an added intake of a D24 dilution of potentiated polyclonal antibodies to angiotensin-converting enzyme (in a dose of 15 drops of alcohol solution 3 times a day) made it possible to lower the patient's systolic pressure to 120-130 mm Hg. The patient had not presented any complaints for 2 months.

C. Patient D., aged 19, had been suffering from therapy-resistant arterial hypertension for 6 months. The use of a C12 dilution of potentiated antibodies to ANGIOTENSIN II in a dose of 1 tablet 2 times a day made it possible to stabilize the patient's condition: no complaints, the blood pressure reached 120/75 mm Hg.

EXAMPLE 30

Potentiated Antibodies to Diuretic Drugs

Potentiated antibodies to FUROSEMIDE (5-(aminosulfonyl)-4-chloro-2-[(2-furanylmethyl)]aminobenzoic acid).

A. Patient D., aged 67, had been taking a course of treatment with FUROSEMIDE for edemata caused by cardiac failure. She complained of nausea and the lack of appetite. Furosemide was discontinued. The recommendation was to start the oral intake of a C30 aqueous solution of potentiated monoclonal antibodies to 5-(aminosulfonyl)-4-chloro-2-[(2-furanylmethyl)]aminobenzoic acid 2 times a day in a dose of 20 ml. A new examination 7 days later revealed the improved appetite, the absence of nausea and edemata.

Potentiated antibodies to HYPOTHIAZIDE (6-chloro-3,4-dihydro-2H-1,2,4-benzothiadiazine-7-sulfonamide-1,1-dioxide).

B. Patient N., aged 64, with established diagnosis of hypertensive disease had been taking HYPOTHIAZIDE. The patient noticed a decrease in the efficacy of the preparation; hence, HYPOTHIAZIDE was discontinued. The recommendation was to start the oral intake of a C200 dilution of a potentiated antiserum to HYPOTHIAZIDE in a dose of 1 tablet 3 times a day, which made it possible to pre-serve the diuretic effect after HYPOTHIAZIDE had been discontinued.

EXAMPLE 31

Potentiated Antibodies to Cardiotropic Drugs

Potentiated antibodies to nitrates.

Potentiated antibodies to NITROSORBIDE (1,4,3,6-dianghydrido-D-glucitol dinitrate).

A. Patient Sh., aged 52, suffering from hypertensive disease complained of headache after the first intake of NITROSORBIDE. In addition to the conventional treatment, the oral intake of a C20 dilution of potentiated antiserum to NITROSORBIDE was prescribed in a dose of 10 ml 3 times a day. Seven days later the patient reported an improved tolerance to NITROSORBIDE and the lessening of pain.

Potentiated antibodies to NITROGLYCEROL.

B. Patient U., aged 71, had been taking NITROSORBIDE (40 mg a day, 4 tablets) for 5 weeks for ischemic heart disease and angina of effort along with NITROGLYCEROL as needed (up to 8-10 tablets a day). Within the last week the dose of NITROSORBIDE was increased to 6 tablets, and that of NITROGLYCEROL, to 15-16 tablets as the angina attacks grew more frequent. The prescription was to take a C6 dilution of potentiated antibodies to NITROGLYCEROL in a dose of 1 tablet 2 times a day. After 5 days of treatment a marked reduction in the frequency of attacks was achieved, which made it possible to reduce the dose of NITROSORBIDE to 4 tablets and that of NITROGLYCEROL to 1-2 tablets a day.

Potentiated antibodies to Cytochromes a+a3.

C. Patient G., aged 39, was admitted to hospital with the diagnosis of hypertensive disease, ischemic heart disease, cardiac failure due to myocardial infarction; he had been treated with intravenous infusions of SODIUM NITROPRUSSIDE (sodium nitrozylpentacyanoferrate) in a dose of 100 mg a day for 4 days. By the $5^{th}$ day the hypotensive effect of the preparation had significantly decreased as sodium cyanide accumulating as a result of SODIUM NITROPRUSSIDE metabolism played an important part in the pharmacological effect of the preparation. (Cyanides act as blockers of the mitochondria respiratory chain at the level of Cytochrome a+ a3). The administration of a C200 dilution of potentiated polyclonal antibodies to CYTOCHROMES a+ a3 in a dose of 1 tablet 3 times a day restored the efficacy of SODIUM NITROPRUSSIDE.

Potentiated antibodies to β-adrenoblockers.

Potentiated antibodies to ATENOLOL (4-[2-hydroxy-3-[(1-methylethyl)amino]propoxy]benzeneacetamide).

D. Patient E., aged 32, complained of episodes of tachycardia caused by overfatigue. Electrocardiography revealed no organic lesions. ATENOLOL was discontinued. The oral intake of a C12 dilution of a potentiated antiserum to ATENOLOL was prescribed. The intake of the preparation in a dose of 1 tablet 2 times a day resulted in a decrease both in the intensity and duration of episodes of tachycardia 5 days after the beginning of treatment.

Potentiated antibodies to ANAPRILIN (PROPRANOLOL) (1-[(1-methylethyl)amino]-3-(1-naphthalenyloxy)-2-propanol).

E. Patient I., aged 54, sought for medical advice for periodic heavy breathing. She presented a history of a regular intake of ANAPRILIN (PROPRANOLOL). The intranasal administration of a C12 dilution of a potentiated solution of monoclonal antibodies to 1-[(1-methylethyl)amino]-3-(1- naphthalenyloxy)-2-propanol in a dose of 0.5 ml 2 times a day was prescribed as monotherapy. A new examination 7 days later showed an improvement of the respiratory function. A conclusion about the efficacy of the homeopathic preparation was drawn.

F. Patient A., aged 57, developed bradyarrhythmia with Morgagni-Adams-Stokes attacks after myocardial infarction. To prevent attacks she took ORCIPRENALINE (½ tablet 6 times a day) and complained of nausea, dryness in her mouth, and the tremor of her hands. The treatment with a D3 dilution of potentiated monoclonal antibodies to ORCIPRENALINE (in a dose of 1 tablet 3 times a day) made it possible to eliminate the unpleasant sensations; the attacks of arrhythmia stopped recurring.

Potentiated antibodies to cardiac glycosides.

Potentiated antibodies to DIGITOXIN ((3β,5β.)-3-[(O-2, 6-dideoxy-β-D-ribo-hexapyranosyl-(1-4)-O-2,6-dideoxy-β-D-ribo-hexopyranosyl)-(1-4)-2,6-didesoxy-β-D-ribo-hexapyranosyl)oxy]-14-hydroxycard-20(22)-enolide).

G. Patient B., aged 68, had been taking a course of treatment with DIGITOXIN for cardiac failure complained of nausea associated with the intake of the preparation. The additional prescription was the oral intake of a C200 dilution of a potentiated preparation of polyclonal antibodies to ((3β, 5β.)-3-[(O-2,6-dideoxy-β-D-ribo-hexopyranosyl-(1-4)-O-2, 6-dideoxy-β-D-ribo-hexopyranosyl)-(1-4)-2,6-dideoxy-β-D-ribo-hexapyranosyl)oxy]-14-hydroxycard-20(22)-enolide) in a dose of 1 tablet 2 times a day. After two days of the treatment the patient noticed the disappearance of nausea. The intake of the homeopathic preparation made it possible to improve the patient's tolerance of DIGITOXIN and to reduce gradually its dose to ¼ of a tablet 2 times a day.

H. Patient Ch., aged 31, with an established diagnosis of chronic cardiac failure caused by rheumatic heart disease had been taking the maintaining dose of DIGITOXIN 0.75 mg a day (3 tablets). She suffered from permanent nausea and periodical vomiting. An attempt to reduce the dose of DIGITOXIN resulted in the enhancement of manifestations of cardiac failure, edema in the first place. With DIGITOXIN discontinued, the patient started receiving a D6 dilution of potentiated antiidiotypic antibodies to DIGITOXIN (in a dose of 1 tablet 3 times a day). Two weeks later the patient's condition was satisfactory: the blood pressure became stable and no manifestations of cardiac failure were observed Potentiated antibodies to antiarrhythmic drugs.

Potentiated antibodies to DISOPYRAMIDE (α-[2-[bis(1-methylethyl) amino]ethyl]-α-phenyl-2-pyridine acetamide).

I. Patient S., aged 35, complained of restlessness and tachycardia. The oral intake of a C200 dilution of potentiated monoclonal antibodies to RYTHMILEN (DISOPYRAMIDE) (α-[2-[bis(1-methylethyl)amino]ethyl]-α-phenyl-2-pyridine acetamide) in a dose of 1 tablet 2 times a day was prescribed. At the new examination the patient presented no complaints for tachycardia.

Potentiated antibodies to RHYTHMONORM.

J. Patient Zh., aged 45, has been taking RHYTHMONORM (Propaphenone) (2[2-hydroxy-3-(propylamino) propoxy]-3-phenyl-propiophen-one), an antiarrhythmic drug of the IC class) in a dose of 150 mg 3 times a day for ventricular extrasystoles. The planned blood test revealed leukopenia ($3.8 \times 10^3/\mu l$) and thrombocytopenia ($170 \times 10^3/\mu l$). Rhythmonorm was discontinued. The administration of a C50 dilution of potentiated antibodies to PROPAPHENONE in a dose of 1 tablet in the morning within 10 days resulted in the normalization of the patient's blood picture with preserved antiarrhythmic effect.

Potentiated antibodies to SOTALOL (N-[4-[1-hydroxy-2-[(1-methylethyl)amino]ethyl]phenyl]methane sulfonamide)

K. Patient D., aged 28, complained of night episodes of pulse intermittence, mild pain in the left part of her thorax. Electrocardiography revealed no organic lesions of the myocardium. After the preceding therapy had been cancelled, the patient started the oral intake of a C30 dilution of potentiated antibodies to SOTALOL (N-[4-[1-hydroxy-2-[(1-methylethyl)amino]ethyl]phenyl]methane sulfonamide) in a dose of 1 tablet at bedtime. During the following 10 days there were no attacks of arrhythmia or pain.

Potentiated antibodies to VERAPAMIL (α-[3-[[2-(3,4-dimetoxyphenyl)ethyl]methylamino]propyl]-3,4-dimetoxy-α-(1-methylethyl)benzene-acetonitryl).

L. Patient K., aged 34, complained of headache, tachycardia, and overfatigue. The examination revealed elevated blood pressure (140/90). The recommendation was to take nasal drops of a C200 aqueous solution of potentiated antibodies to VERAPAMIL (α-[3-[[2-(3,4-dimetoxyphenyl) ethyl]methylamino]propyl]-3,4-dimetoxy-α-(1-methylethyl)benzeneacetonitryl) in a dose of 0.5 ml at bedtime. The patient reported feeling better, his blood pressure dropped to the normal level after two days of the treatment. It was recommended to continue the course of treatment.

M. Patient Z., aged 55, with an established diagnosis of ischemic heart disease, angina of effort, atrial extrasystoles, and tachycardia (90 beats/min) had been taking 240 mg of ISOPTIN daily in a dose of 1 tablet 3 times a day. The patient complained of constipation not associated with the regimen faults or diet changes. The intake of potentiated antibodies to ISOPTIN LM 50 in a-dose of 1 tablet 2 times a day resulted in the normalization of the bowel function without interfering with the basic therapeutic effect of ISOPTIN. Later on, the dose of ISOPTIN was gradually reduced and finally ISOPTIN was discontinued. The patient's condition remained satisfactory for two months against the background of therapy with antibodies.

N. Patient D., aged 63, with the diagnosis of progressive chronic cardiac failure was treated at the cardiology unit of a clinical hospital (intravenous infusion of 30 mg of MILRINONE daily in a dose of 10 ml 3 times a day). As the patient's myocardial contractive capacity and hemodynamic indices were gradually improving, there appeared complaints of heartache. ECG revealed signs of myocardial ischemia. The treatment with a C12 dilution of potentiated antibodies to MILRINONE in a-dose of 1 tablet 3 times a day was started. Heartache disappeared, the ECG pattern returned to normal, and the treatment with MILRINONE was continued. Gradually the preparation was discontinued and the patient was switched to the treatment with antibodies alone in a dose of 1 tablet a day. The patient's condition is satisfactory.

O. Patient S., aged 58, had been taking MILRINONE for 1.5 years for chronic cardiac failure. In the course of the period of treatment the daily dose had to be increased from 10 to 30 mg because of the developing resistance to the preparation. After the prescription of a C30 dilution of potentiated antibodies to the enzyme PHOSPHODIESTERASE in a dose of 1 sublingual tablet once a day to be taken in the morning the patient's condition markedly improved: the ECG signs of myocardial overload and ischemia became less pronounced and peripheral edema disappeared. Three months of a regular intake of potentiated antibodies made it possible to reduce the daily dose of MILRINONE to 10 mg.

Potentiated antibodies to CORDARON.

P. Patient S., aged 50, had been suffering from stable angina of effort with paroxysms of ciliary arrhythmia for 2 years. From the onset of his illness the patient had been taking CORDARON in a dose of 600 mg a day (3 tablets). After a year of the treatment an increase in the frequency of paroxysms of ciliary arrhythmia was registered. Paroxysms occurred every day; an increase in the dose of CORDARON as well as the administration of other antiarrhythmic drugs was inefficient. No physical or emotional strain accounted for the paroxysms; the paroxysms cease spontaneously. This condition seemed indicative of a thyroid function disorder; the patient was examined by an endocrinologist who established the diagnosis of thyrotoxicosis of a moderate severity. The patient's thyroid profile looked as follows: TTH 1.29 mIU/l (the normal range is 0.45-6.2), total T4 180.3 nmol/l (the normal range is 39-155), T33.2 nmol/l (the normal range is 1.2-3.1). The treatment with a C24 dilution of potentiated antibodies to CORDARON in a dose of 1 tablet 3 times a day was started. Within a month the euthyroid state was achieved. Now the patient takes CORDARON in a dose of 100 mg a day (¼ of a tablet 2 times a day), paroxysms of ciliary arrhythmia are rare (about once a week).

EXAMPLE 32

Potentiated Antibodies to Hypocholesterolemic Drugs

Potentiated antibodies to PROBUCOL.

A. Patient K., aged 62, with the diagnosis of-coronary sclerosis, angina of effort, and hypercholesterolemia had been taking PROBUCOL for 2 months along with antianginal drugs (in a dose of 500 mg 2 times a-day at mealtime). The patient complained of dyspepsia, meteorism in the first place, the onset of which dated back to one month after he had started taking the preparation. The administration of a C30 dilution of potentiated antibodies to PROBUCOL in a dose of 1 tablet a day controlled the patient's intestinal disorders. The daily dose of PROBUCOL was reduced by 50%.

Potentiated antibodies to NICOTINIC ACID.

B. Patient L., aged 58, had been taking NICOTINIC ACID in a dose of 4.0 g a day for atherosclerosis of peripheral vessels (especially pronounced in the lower extremities). The patient complains of hot flashes and redness of the face. The intake of a C12 dilution of potentiated antibodies to nicotinic acid in a-dose of 1 tablet 3 times a day improved the patient's tolerance of the preparation and made it possible to reduce its dose to 1.0 g a day.

Potentiated antibodies to PRAVASTATIN.

C. Patient F., aged 57, suffered from ischemic heart disease and primary hypercholesterolemia. He had been taking PRAVASTATIN for 3 months in a dose of 20 mg at bedtime along with NITROGLYCEROL (up to 5-6 tablets a day for angina attacks). In the course of the last 10-15 days he noticed the development of muscular weakness. The biochemical analysis of the patient's blood revealed transaminase levels elevated to the upper bound (ALT 50 IU/l, AST 45 IU/l). The administration of a C200 dilution of potentiated antibodies to PRAVASTATIN in a dose of 1 tablet once a day resulted in the improvement of the patient's condition of health, his blood transaminase level lowered (ALT 26 IU/I, AST 21 IU/1). Angina attacks became less frequent and the patient's intake of nitroglycerol tablets reduced to 1-2 tablets a day.

Potentiated antibodies to ETOFIBRATE.

D. Patient P., aged 55, with an established diagnosis of ischemic heart disease and hypercholestrolemia had been taking ETOFIBRATE (in a dose of 500 mg once a day) following his physician's advice. The patient stated that after a month of the treatment with this preparation he began to suffer from abdominal pain and meteorism. The intake of a C30 dilution of potentiated antibodies to ETOFIBRATE in a dose of 1 tablet a day resulted in the normalization of the patient's condition. The dose of ETOFIBRATE was reduced by 50%. The patient's lipid metabolism indices remained within normal limits.

Potentiated antibodies to ORLISTATE.

E. Patient O., aged 59, suffered from diabetes mellitus, Type 2, and obesity (height 160 cm, body weight 100 kg) and had been taking 120 mg of ORLISTATE (the inhibitor of gastric lipases) 3 times a day at meals. Within several months of the treatment combined with low-calorie diet the patient body weight decreased by 7 kg; however, the patient complained of poor feeling, which was manifested by meteorism and imperative rectal tenesmus. The prescription of a C200 dilution of potentiated polyclonal antibodies to ORLISTATE in a dose of 1 tablet a day improved the patient's tolerance of the preparation, decreased her blood sugar level, and made it possible to reduce the dose of insulin.

EXAMPLE 33

Potentiated Antibodies to Antitumor Drugs

Potentiated antibodies to DOXORUBICIN [(8S-cis)-10-[(3-amino-2,3,6-trideoxy-α-L-Iyxo-hexopyranosyl)oxy]-7,8,9,10-tetrahydro-6,8,11-trihydroxy-8-(hydroxyacetyl)-1-methoxy-5,12-naphtacenedione].

A. Patient P., aged 61, had been receiving a course of chemotherapy with DOXORUBICIN [(8S-cis)-10-[(3-amino-2,3,6-trideoxy-α-L-lyxo-hexopyranosyl)oxy]-7,8,9,10-tetrahydro-6,8,11-trihydroxy-8-(hydroxyacetyl)-1-methoxy-5,12-naphtacenedione] for lung cancer but had to stop taking the medication because of nausea and vomiting. The prescription was to combine the administration of the cytostatic drug with the oral intake of a C6 solution of potentiated monoclonal antibodies to DOXORUBICIN. As a result the nausea subsided, which made it possible to continue chemotherapy. Later on, DOXORUBICIN was discontinued and the patient was put on potentiated anti-bodies alone. The patient is feeling well and X-ray findings show the arrest of tumor growth.

Potentiated antibodies to CISPLATIN (cis-diaminodichloriplatinum).

B. Patient D., aged 57, complained of cramps in her lower extremities during the process of chemotherapy with CISPLATIN for ovarian cancer. A C12 dilution of potentiated monoclonal antibodies to cis-diaminodichlorplatinum in a dose of 2 ml intramuscularly once a day was prescribed. This drug made it possible not only to control cramps and improve the patient's tolerance of cisplatin but also to reduce the dose of the latter by 50%.

Potentiated antibodies to METHOTREXATE (N-[4-[[(2,4-diamino-6-pteridinyl)methyl]methylamino]benzoyl]-L-glutamic acid).

C. Patient P., aged 9, was admitted to hospital for acute lymphoblastic leucosis. In the course of chemotherapy with METHOTREXATE the patient started complaining of severe headaches and nausea. The treatment with a D12 dilution of a potentiated antiserum to METHOTREXATE in a dose of 1 tablet 2 times a day was begun. Two days later, with continued chemotherapy, the patient reported that his headaches disappeared and nausea subsided. He kept taking the potentiated preparation. Two months later the patient's condition was satisfactory and METHOTREXATE was discontinued. Four months later, against the background of continued monotherapy with antibodies, the patient's lymphogram was close to normal.

Potentiated antibodies to THALIDOMIDE.

D. Patient U., aged 42, suffered from multiple myeloma. Two bone marrow transplantations resulted in short remissions. The third transplantation did not lead to a remission; the blood MIG (myeloma immunoglobulin, a protein marker of tumor cells) level was rising. The treatment with THALIDOMIDE made it possible to achieve stable remission and the depression of the blood MIG level; however the patient started complaining of weakness, drowsiness constipation, and numbness sensation in his extremities. It was suggested to use the intranasal administration of a C30 dilution of potentiated antibodies to THALIDOMIDE in a dose of 1 ml 3 times a day as additional treatment. After a week of treatment with antibodies the patient started feeling better, no signs of the progressive course of his myeloma were observed, and the blood MIG level kept falling dramatically.

Potentiated antibodies to VERAPAMIL.

E. Patient Sh., aged 29, with an established diagnosis of small-cell carcinoma of his left lung was going through a course of chemotherapy with cisplatin and methotrexate. The patient was also taking VERAPAMIL (a calcium channel blocker) in order to enhance the tumor cell sensitivity to the treatment. After a month of treatment, there appeared symptoms of cancer progression. Added to the treatment protocol was the intake of a C200 dilution of potentiated anti-bodies to VERAPAMIL in a dose of 1 tablet-a day. The patient started feeling better and his X-ray image showed the arrest of tumor progression.

Potentiated Antibodies to TOPOISOMERASE II

F. Patient T., aged 40, with an established diagnosis of lung carcinoma underwent two courses of treatment with CISPLATIN and ETOPOSIDE, after which clinical and X-ray findings revealed the tumor's primary resistance to antitumor drugs. The third course of the treatment with cytostatic drugs was combined with the administration of a C30 dilution of potentiated antibodies to topoisomerase II in a dose of 1 sublingual tablet once a day. The patient started feeling better and X-ray patterns revealed the arrest of tumor progression.

Potentiated antibodies to PROSPIDINE.

G. Patient R. aged 37 was undergoing hospital treatment with PROSPIDINE (300 mg in the form of intramuscular injections 3 times a week) as monochemotherapy for T lymphoma of the skin. A decrease in the area of skin lesions (by 30%) along with improved laboratory test data allowed the treatment to be regarded as efficient; however, there was no further progress in the patient's condition. The treatment was supplemented with a C200 dilution of potentiated anti-bodies to PROSPIDINE in a dose of 1 tablet a day. The area of skin lesions reduced by another 40%.

Potentiated Antibodies to Hormone Antagonists TAMOXIFEN ((Z)-2-[4-(1,2-diphenyl-1-butenyl)phenoxy]-N,N-dimethyl-ethan-amine).

H. Patient I., aged 47, was taking a course of chemotherapy with TAMOXIFEN ((Z)-2-[4-(1,2-diphenyl-1-butenyl)phenoxy]-N,N-dimethylethan-amine) for breast cancer; she complained of dizziness and nausea. The intranasal administration of 0.5 ml of a C30 aqueous solution of potentiated monoclonal antibodies to TAMOXIFEN 3 times a day was prescribed. The patient's nausea subsided to a bearable level.

Potentiated antibodies to FLUTAMIDE (2-methyl-N[4-nitro-3-(trifluormethyl) phenyl]propanamide).

I. Patient U., aged 41, complained of fatigue and the loss of libido and potency. The administration (in the form of intranasal drops at bedtime) of 0.5 ml of a C12 solution of a potentiated antiserum to FLUTAMIDE (2-methyl-N[4-nitro-3-(trifluormethyl)phenyl]propanamide). After 10 days of the treatment the patient stated the improvement of his ability to work and sexual activity. It was recommended to continue the course of treatment.

EXAMPLE 34

Potentiated Antibodies to Regulators of the Blood Coagulation Process

Potentiated antibodies to HEPARIN (mucopolysaccharide of a polysulfuric acid ester).

A. Patient M., aged 59, complained of superficial pains in her lower extremities. The diagnosis of trombophlebitis was established; aqueous compresses with a D6 solution of a potentiated antiserum to heparin at bedtime were recommended. After 5 procedures the pain and local redness subsided.

Potentiated antibodies to TICLOPIDINE (5-[2-chlorophenyl)methyl]-4,5,6,7-tetrahydrothieno[3,2-c]pyridine).

B. Patient K., aged 63, complained of moderate heartaches. The diagnosis of ischemic heart disease was made. The oral intake (at bedtime) of 20 ml of a C30 potentiated solution of polyclonal antibodies to TICLOPIDINE (5-[2-chlorophenyl)methyl]-4,5,6,7-tetrahydrothieno[3,2-c]pyridine) C30 in a dose of 1 tablet 3 times a day was prescribed. After 3 months of the treatment no worsening of the disease was observed. The conclusion was drawn about the efficiency of the potentiated preparation for the prevention of ischemic heart disease.

EXAMPLE 35

Potentiated Antibodies to Hormonal Agents

Potentiated antibodies to INSULIN.

A. Patient R., aged 45, with an established diagnosis of diabetes mellitus Type 1 complained of ulcer of the skin integument of his lower extremities. Local rubbing with a C30 dilution of a 30% alcoholic solution of an antiserum to insulin was included into the scheme of combined therapy. Epithelization of skin integument lesions was achieved.

B. Patient D., aged 52, with an established diagnosis of diabetes mellitus Type 2 had an excessive body weight. His fasting blood glucose level was 10 mmol/l. The glucose level correction could not be achieved by diet and synthetic antihyperglycemic agents. Within 3 months the daily dose of insulin increased from 5 to 25 units. The treatment with a C200 dilation of potentiated monoclonal antiidiotypic antibodies to insulin in a dose of 1 tablet a day was started. Two weeks later the patient's sensitivity to insulin increased; the dose of insulin was reduced to 5 units, the fasting blood glucose level reached 5 mmol/l. After 2 months of the treatment insulin was discontinued and the patient was switched to therapy with antibodies alone.

C. Patient I., aged 48, suffered from a severe form of diabetes mellitus with a high degree of insulin resistance (the patient needed up to 128 units a day). The treatment with a C30 dilution of a potentiated antiserum to the insulin-like growth factor in a dose of 1 tablet 3 times a day resulted in a marked improvement of the patient's condition. His blood-glucose level dropped to 16 mmol/l. The daily dose of insulin was reduced by 50%.

Potentiated antibodies to ESTRADIOL.

D. Patient B., aged 34, was admitted to the neurology department of a clinical hospital with complaints of rapid uncontrollable movements in her right extremities. These symptoms developed after a common cold. The patient gave no history of rheumatic fever. At the time of admission the patient was pregnant for the second time (the $21^{st}$-$22^{nd}$ week); she suffered from early gestosis; there had been no complications in the course of her first pregnancy. Before deciding to have another baby the patient had been taking oral contraceptives. The patient was slightly euphoric. The memory and intellect were unimpaired. Her arterial blood pressure was 120/80 mm Hg. Hyperkinesias of her right extremities, predominantly in her arm and hand were found. Gynecological examination did not reveal any indication for the termination of pregnancy. The treatment with a C200-dilution of a potentiated form of antibodies to ESTRADIOL in a dose of 1 tablet a day was started; a week later the symptoms of hyperkinesia disappeared. The patient had an uncomplicated delivery at term; her baby was in good health.

Potentiated antibodies to GLUCAGON.

Patient T., aged 64, complained of bradycardia and arterial hypotension upon admission; she had been taking ATENOLOL. The oral administration of a C12 dilution of potentiated polyclonal antibodies to GLUCAGON in a dose of 1 tablet 3 times a day was prescribed. Within 24 hours the normalization of the cardiac rhythm and arterial pressure was achieved.

Potentiated antibodies to TRIIODOTHYRONINE (LIO-THYRONINE) (O-(4-hydroxy-3-iodophenyl)-3,5-diiodo-L-thyrosine).

E. Patient D., aged 36, complained of tachycardia and heartaches. The examination revealed no organic disorders. The oral intake of a C12 dilution of potentiated polyclonal antibodies to TRIIODOTHYRONINE (O-(4-hydroxy-3-iodophenyl)-3,5-diiodo-L-thyrosine) in a dose of 1 tablet 3 times a day was prescribed. After 5 days of the treatment the normalization of cardiac rhythm and the disappearance of pain were achieved.

Potentiated antibodies to CALCITONIN.

F. Patient I., aged 58, complained of pain in her tubular bones and soft tissues of her extremities. The examination confirmed the diagnosis of osteoporosis. The intranasal administration of 0.5 ml a C24 dilution of a potentiated monospecific antiserum to CALCITONIN twice a day was prescribed within the framework of combined therapy. Three days later the patient started feeling better and reported the lessening of pain.

Potentiated antibodies to the SOMATOTROPIC HORMONE.

G. Patient Ch., aged 56, had been taking a course of treatment for obesity. Because of the oral administration of a C15 dilution of potentiated monoclonal antibodies to the somatotropic hormone in a dose of 1 tablet 3 times a day together with a diet the patient had lost 4 kilograms within 10 days; the dieting became easier.

Potentiated antibodies to STEROID HORMONES.

Potentiated antibodies to HYDROCORTISONE (113)-11,17,21-trihydroxypregn-4-ene-3,20-dione).

I. Patient Ts., aged 29, a welder by profession complained of sharp pain in his eyes. Twice doses of eye drops containing a C12 aqueous solution of a potentiated antiserum to HYDROCORTISONE (11β)-11,17,21-trihydroxypregn-4-ene-3,20-dione) made it possible to eliminate painful sensations within 24 hours.

Potentiated antibodies to DEXAMETHASONE (11β,16α)-9-fluoro-11,17,21-trihydroxy-16-methylpregna-1,4-diene-3,20-dione).

J. Patient D., aged 39, complained of itching in his nasopharynx. After intranasal administration of 1 ml of a C12 dilution of a potentiated solution of monoclonal antibodies to DEXAMETHASONE (11β,16α)-9-fluoro-11,17,21-trihydroxy-16-methylpregna-1,4-diene-3,20-dione) itching disappeared.

Potentiated antibodies to TESTOSTERONE ((173)-17-hydroxyandrost-4-en-3-one).

K. Patient A., aged 41, complained of the lowering of potency. The examination revealed a moderate degree of obesity and no organic lesions of the central nervous system. A course of treatment with a C6 dilution of potentiated monoclonal antibodies to TESTOSTERONE to be taken by mouth in a dose of 1 tablet 3 times a day was proposed. At his next visit to the physician four weeks later the patient stated that his sexual performance improved and sexual activity enhanced. The patient had lost 5 kg; he tolerated well his food regimen under the conditions of the preparation intake. It was recommended to continue the course of treatment.

EXAMPLE 36

Potentiated Antibodies to Nervous System Mediators

Potentiated antibodies to ACETYLCHOLINE (2-(acetyloxy)-N,N,N-trimethyl-ethaneaminium).

A. Patient Yu., aged 58, complained of constipation. The intranasal administration of 0.5 ml of a C50 dilution of a potentiated solution of antibodies to ACETYLCHOLINE (2-(acetyloxy)-N,N,N-trimethylethaneaminium) 4 times a day was recommended. The stool was back to normal 24 hours after the intake of the preparation.

Potentiated antibodies to NORADERNALINE.

B. Patient D., aged 71, complained of dizziness and bradycardia. The examination revealed hypotension (100/65 mm Hg). The oral intake of 10 ml of an antiserum to noradrenaline in a potency of C14, 3 times a day was prescribed. At his next visit to the physician 6 days later the patient reported feeling better and not suffering from dizziness anymore; his blood pressure was 110/75 mm Hg. It was recommended to continue the course of treatment.

Potentiated antibodies to DOPAMINE.

C. Patient L., aged 69, complained of tremor and gait disorders. The patient had had a long-time history of treatment with neuroleptics for schizophrenia. The treatment was supplemented with a C15 dilution of potentiated polyclonal antibodies to dopamine (oral intake, 1 tablet 3 times a day). Within 4 days the tremor disappeared and no neuroleptic manifestations were observed.

Potentiated antibodies to SEROTONIN (5-hydroxytriptamine).

D. Patient G., aged 41, complained of the worsening of mood and apathy. The intake of a C1000 dilution of a potentiated solution of monoclonal antibodies to (serotonin) in the form of drops in a dose of 1 ml twice a day was proposed. Seven days later the patient reported the improvement of mood and the enhanced motivation to labor. It was recommended to continue the course of treatment.

Potentiated antibodies to ASPARTIC ACID (L-aspartic acid).

E. Patient N., aged 75, complained of tremor of extremities. The examination revealed no organic lesions of the nervous system. The oral intake of a C200 dilution of a potentiated solution of antibodies to aspartic acid in a dose of 1 tablet 3 times a day was recommended. A new examination two days later showed the absence of tremor.

Potentiated antibodies to GLUTAMIC ACID (L-glutamic acid).

F. Patient M., aged 29, complained of cramps in the lower extremities during sleep. The administration of potentiated polyclonal antibodies to L-glutamic acid in a dose of 1 tablet by mouth at bedtime resulted in a decrease in the frequency and intensity of convulsions.

Potentiated antibodies to GLYCINE.

G. Patient P., aged 58, complained of restlessness and sleeping disorders. The oral intake of a C1000 dilution of potentiated antibodies to GLYCINE in a dose of 1 tablet at bedtime was recommended; within two days the patient's sleep became normal.

EXAMPLE 37

Potentiated Antibodies to Mediators of Inflammation and Allergy

Potentiated antibodies to PROSTAGLANDINS.

Potentiated antibodies to MISOPROSTOL (methyl ester of (11α,13E)-(+−)-11,16-dihydroxy-methyl-9-oxoprost-13-en-1-ic acid).

A. Patient K., aged 41, complained of pain in the epigastic area after meals. The oral intake of a C50 dilution of a potentiated solution of polyclonal antibodies to MISOPROSTOL (methyl ester of (11α,13E)-(++11,16-dihydroxy-methyl-9-oxoprost-13-en-1-ic acid) in a dose of 1 tablet before meals was recommended. At his new visit to the physician seven days later the patient reported the elimination of pain.

Potentiated antibodies to KININS.

B. Potentiated antibodies to BRADYKININ.

Patient N., aged 15, complained of dry cough. The administration of potentiated monoclonal antibodies to bradykinin in the form of nasal drops in a dose of 0.5 ml 3 times a day resulted in the disappearance of cough within 2 days.

Potentiated antibodies to HISTAMINE (1H-imidazole-4-ethanamine).

C. Patient Ts., aged 27, complained of severe itching of insect bites. Within the framework of combined therapy compresses with a C30 solution of potentiated antibodies to histamine were applied to the sites of lesions. The next day the redness subsided and the itching disappeared.

EXAMPLE 38

Potentiated Antibodies to Vitamins, Substances with Vitamin-Like Action, and Bioflavonoids A. Patient A., aged 51, had been taking rather large doses of ascorbic acid (5-6 g daily) with health-improvement purposes following his friends' advice. He was admitted to hospital with an attack of renal colic. The pain was controlled with spasmolytic drugs and alkaline solutions. Laboratory blood tests showed high glucose content (9 mmol/l, the normal range being from 3.3 to 5.5 mmol/l). The patient had never consulted endocrinologist and had no family history of diabetes; therefore, the toxic effect of high doses of ascorbic acid upon the pancreas was suggested as the cause of the patient's elevated blood sugar content. The treatment with potentiated antibodies to ascorbic acid in a dose of 1 tablet 3 times a day was started. Within two weeks the fasting blood glucose content dropped to 6 mmol/l.

Potentiated antibodies to THIAMINE (3-[(4-amino-2-methyl-5-pyrimidinyl)methyl]-5-(2-hydroxyethyl)-4-methylthiazolium chloride).

B. Patient V., aged 57, complained of pain in her left thigh. The examination confirmed the diagnosis of neuralgia. A C200 dilution of a potentiated solution of monoclonal antibodies to THIAMINE (3-[(4-amino-2-methyl-5-pyrimidinyl)methyl]-5-(2-hydroxyethyl)-4-methylthiazolium chloride) in a dose of 1 tablet twice a day was recommended. After 6 days of the treatment the lessening of the pain intensity was achieved. A conclusion about the efficiency of such therapy was drawn.

Potentiated antibodies to NICOTINIC ACID (3-pyridinecarboxylic acid).

C. Patient R., aged 48, complained of hot flashes and tachycardia after the intake of nicotinic acid she had been receiving for atherosclerosis. The oral intake of a C30 dilution of a potentiated solution of monoclonal antibodies to 3-pyridinecarboxylic acid in a dose of 1 tablet twice a day was recommended. The patient noticed the subsidence of her tachycardia, which allowed the antihypercholesterolemic therapy to be continued.

Potentiated antibodies to TROXERUTIN (2-[3,4-(bis(2-hydroxyethoxy)phenyl]-3-[[6-O-(6-deoxy-α-L-mannosopyranoz-yl)-β-D-glucopyranozyl]oxy]-5-hydroxy-7-(2-hydroxyethoxy)-4H-1-benzopyranone-4).

D. Patient U., aged 42, complained of pain after she had bruised her thigh. The examination revealed a large hematoma. Compresses with a C6 dilution of an aqueous solution of a potentiated antiserum to TROXERUTIN were recommended. A new examination two days later showed the shrinking of the hematoma; the patient felt no pain.

Potentiated antibodies to DIHYDROERGOCRISTINE.

E. Patient K., aged 29, had been taking 1 lozenge of ANAVENOL (the preparation composed of an α-adrenolytic agent DIHYDROERGOCRISTINE, ESCULINE, and RUTOZIDE) 3 times a day for varicose veins in her legs developed during pregnancy and the postpartum period. The edema and heavy feeling in the legs were lessening but the patient started complaining of headaches and dizziness. Anavenol was discontinued. The treatment with a C30 dilution of potentiated antibodies to dihydroergocristine in a dose of 1 tablet twice a day was begun. The patient's condition of health kept improving, headaches and dizziness disappeared. Two months later a marked regression of varicosity was registered.

Potentiated antibodies to DETRALEX bioflavonoid (contains a combination of diosmine and hesperedin).

F. Patient V., aged 42, an operation nurse, had been suffering from varicose veins in her legs for 5 years. Following her doctor's recommendations, she started taking DETRALEX (1 tablet twice a day). She complained of dyspepsia not associated with diet faults. The treatment with a C30 dilution of potentiated antibodies to each component alternately (every other day) in a dose of 1 tablet daily was initiated. The patient started feeling much better after one week of the intake of the antibodies. Six weeks later no symptoms of varicose veins were seen.

Potentiated antibodies to VITAMIN A. (trans-9,13-dimethyl-7-(1,1,5-trimethylcyclohexen-5-yl-6)-nonatetraen-7,9,11,13-ol).

G. Patient K., aged 26, complained of headache, running nose and artralgia. In order to raise the patient's immunity, the oral intake of a C200 dilution of a potentiated antiserum to VITAMIN A (trans-9,13-dimethyl-7-(1,1,5-trimethylcyclohexen-5-yl-6)-nonatetraen-7,9,11,13-ol) in a dose of 1 tablet a day was prescribed. At his next visit three days later the patient reported feeling well.

Potentiated antibodies to VITAMIN D (ERGOCALCIFEROL) (5Z,7E,22E)-9,10-secoergosta-5,7,10(19),22-tetraen-3-ol).

H. Patient N., aged 55, complained of pain in his hands not associated with physical strain and cramps in his lower extremities. The recommendation was: the intake of a C200 dilution of potentiated solution of an antiserum to VITAMIN D (ERGOCALCIFEROL) (5Z,7E,22E)-9,10-secoergosta-5,7,10(19),22-tetraen-3-ol) in a dose of 1 tablet 2 times a day in combination with preparations of calcium. After three weeks of the therapy the lessening of pain and the disappearance of convulsive reactions were observed. It was recommended to continue the course of treatment.

Potentiated antibodies to VITAMIN E (3,4-dihydro-2,5,7,8,-tetramethyl-2-(4,8,12,trimethyltridecyl)-2H-1-benzopyranol acetate).

I. Patient A., aged 43, complained of fatigability and muscle weakness. After a weeklong course of treatment with a C30 dilution of potentiated monoclonal antibodies to VITAMIN E (3,4-dihydro-2,5,7,8,-tetramethyl-2-(4,8,12,-trimethyltridecyl)-2H-1-benzopyranol acetate) in a dose of 1 tablet 3 times a day the patient stated an increase in his ability to work and the improvement of mood.

EXAMPLE 39

Potentiated Antibodies to Immunomodulators and Cytokines

Potentiated antibodies to interferon.

A. Patient P., aged 34, complained of rhinitis and pain in his nasopharynx. The diagnosis of acute respiratory viral infection was established. A double administration of intranasal drops of a potentiated C12 aqueous solution of monoclonal antibodies to γ-interferon resulted in the normalization of the patient's condition of health within two days. A conclusion was made that the antibodies featured the antiviral effect.

Potentiated antibodies to interleukins.

Potentiated antibodies to aldesleukin (interleukin 2).

B. Patient M., aged 42, had been running course of treatment for the exacerbation of chronic bronchitis. The oral intake of a C30 dilution of potentiated monoclonal antibodies to interleukin 2 in a dose of 1 tablet 3 times a day resulted in the normalization of the body temperature three days after the beginning of the treatment with the homeopathic preparation. The recommendation was to take the preparation in a dose of 1 tablet once a day for three months. Catamnesis: no exacerbations of chronic bronchitis occurred during 8 months of medical observation. A conclusion was made that the antibodies possessed an immunity boosting effect.

Potentiated antibodies to colony-stimulating factors.

C. Patient L., aged 23, complained of dizziness. He had a long (20 days) history of the intake of baralgin containing a pyrazolone derivative with a hemopoiesis-suppressing effect. The oral intake of a C200 dilution of potentiated polyclonal antibodies to filgrastim (colony-stimulating factor) in a dose of 1 tablet 3 times a day was recommended; this made it possible to achieve normal counts of neutrophiles and erythrocytes within 6 days after the beginning of treatment. Conclusion: the antibodies possessed a hemopoietic effect.

Potentiated antibodies to LEVAMIZOL. ((S)-2,3,5,6-tetrahydro-5-phenylmidazo[2,1-b]thiazole).

D. Patient K., aged 41, was hospitalized with an established diagnosis of maxillary sinusitis. The administration of a C12 dilution of potentiated monoclonal antibodies to LEVAMIZOL ((S)-2,3,5,6-tetrahydro-5-phenylmidazo[2,1-b]thiazole) in the form of nasal drops in a dose of 0.5 ml twice a day made it possible to control headache and to return the body temperature to the normal level within three days. It was the immunostimulating effect of potentiated antibodies that accounted for such results.

E. Patient P., aged 53, suffered from the exacerbation of her hypertensive disease; the blood pressure reached 180/100 mm Hg. As she used to take DIBAZOL as part of her antihypertension treatment, there was made a suggestion to start treatment with a C30 dilution of potentiated polyclonal antibodies to DIBAZOL in a dose of 1 tablet twice a day. Within three days her blood pressure dropped to 150/80 mm Hg. The treatment with antibodies was continued. Despite the fact that there was an epidemic of flu in the city, to which all the members of the patient's family succumbed, the patient never developed any symptoms of viral respiratory infection. A conclusion was drawn about the hypotensive and immunostimulating effects of the antibodies.

Potentiated antibodies to immunodepressant drugs.

F. Patient D., aged 27, complained of redness and itching of her hands after a contact with a synthetic detergent. Her condition was diagnosed as allergic dermatitis. The oral intake of a C200 dilution of a homeopathic solution of monoclonal antibodies to CYCLOSPORIN in a dose of 1 tablet twice a day lessened the severity of the allergic reaction within 24 hours.

G. Patient A., aged 28, had been staying at hospital for basic antirheumatic therapy-resistant rheumatoid arthritis. The patient had been treated with CYCLOSPORIN A (CsA) (2.5 mg/kg per diem) for 4 months with good therapeutic effect. A routine blood test showed an elevated creatinine level; the patient's blood pressure was raising in the course of the last week (160/90 mm Hg). The danger of the exacerbation of arthritis and the inefficiency of other medications precluded cancellation of treatment with CsA. The dose of CsA was reduced to 1.5 mg/kg per diem and a C200 dilution of potentiated antibodies to CsA was prescribed in a dose of 1 tablet twice a day. After a week of the treatment the creatinine content went back to normal, the blood pressure dropped to 120/75 mm Hg. The stable antirheumatic effect of CsA persisted along with the patient's good tolerance of it. Later CsA was discontinued. The intake of potentiated anti-bodies was continued in a dose of 1 tablet every day. Catamnesis 6 months later: rheumatoid arthritis in the phase of remission.

H. Patient L., aged 47, complained of lumbar pain. After the diagnosis of lumbosacral radiculitis had been established, a recommendation was made: the oral intake of a C12 dilution of polyclonal antibodies to CHONDROITIN SULFATE in a dose of 1 tablet 3 times a day along with conventional anti-inflammatory drugs. After two days of the treatment the pain syndrome subsided. Monotherapy with antibodies made it possible to begin to control the manifestations of radiculopathy within 7 days.

I. Patient O., aged 40, had been participating in the elimination of the consequences of the Chernobyl catastrophe; he suffered from radiation cataract of both eyes. The patient used to take AZAPENTACENE (2 drops into both eyes 5 times a day) to good effect; however he complained to the attending oculist of an itching and burning sensation in his eyelids. The suggestion was to discontinue the administration of the preparation temporarily and to use a D12 dilution of antibodies to AZAPENTACENE in a dose of 1 tablet twice a day. When the irritation of the patient's eyelids had subsided, the treatment with potentiated antibodies was successfully continued.

EXAMPLE 40

Potentiated Antibodies to Antibiotics and Antiparasite Drugs

Potentiated antibodies to CIPROFLOXACIN (1-cyclopropyl-6-fluoro-1,4-dihydro-4-oxo-7-(1-piperazinyl)-3-quinolinecarboxylic acid).

A. Patient Ts., aged 26, complained of cough and pain in his nasopharynx. Physical examination showed a rise in the body temperature to 37.1° C. After two days of the intake of a solution of potentiated antibodies to CIPROFLOXACIN (1-cyclopropyl-6-fluoro-1,4-dihydro-4-oxo-7-(1-piperazinyl)-3-quinolinecarboxylic acid) in a dose of 10 drops 3 times a day the patient's condition normalized and the body temperature dropped to 36.7° C.

Potentiated antibodies to METRONIDAZOLE (2-methyl-5-nitro-1H-imidazole-1-ethanol).

B. Patient A., aged 32, complained of nausea after metronidazol intake. The additional administration a of C12 dilution of potentiated monoclonal antibodies to 2-methyl-5-nitro-1H-imidazole-1-ethanol in a dose of 1 tablet 3 times a day made it possible to eliminate nausea and continue the treatment.

C. Potentiated antibodies to CEFEPIM ([[7-[[(2-amino-4-thiazolyl)(metoxyimino)acetyl]amino]-2-carboxy-8-oxo-5-thia-1-azabicyclo[4.2.0]oct-2-en-3-yl]methyl]-1-methylpyrrolidinium hydroxide).

Patient E., aged 36, complained of pain in his knee joints and tonsillitis. The diagnosis of rheumatoid arthritis was established earlier; however, concomitant duodenal ulcer precluded the administration of anti-inflammatory drugs. The recommendation was to take drops of a solution (a D24 dilution) of an antiserum to the antibiotic CEFEPIM ([[7-([(2-amino-4-thiazolyl) (metoxyimino)acetyl]amino]-2-carboxy-8-oxo-5-thia-1-azabicyclo[4.2.0]oct-2-en-3-yl]methyl]-1-methylpyrrolidinium hydroxide) 3 times a day. Five days later the inflammatory reaction subsided and tonsillitis disappeared.

D. Patient Zh., aged 33, was directed to the proctology unit of a clinical hospital with an established diagnosis of perianal abscess. Within the framework of therapy the patient was receiving AMOXYCLAV (a combination of semisynthetic penicillin amoxycillin and clavulonic acid, an inhibitor of β-lactamases), 1 tablet 3 times a day. The patient used to take various antibiotics on his own initiative and without system, including phenoxymethylpenicillin. Along with the amelioration of his general condition (the lowering of the body temperature, the lessening of pain, and the reduction of the white blood count), the patient started complaining of nausea. Following his doctor's advice, the patient began to take AMOXYCLAV at meals; however, nausea persisted. A 7-days' course of the treatment with a C6 dilution of potentiated antibodies to 6-aminopenicillanic acid (common for all penicillins) in a dose of 1 tablet 3 times a day was carried out. The tolerance of the preparation improved; the patient presented no complaints, no indications for surgical treatment were seen; as the blood count and the body temperature were back to normal, the patient was discharged from hospital under local polyclinic observation. Recommendations for the regimen and further treatment were given.

E. Patient V., aged 34, suffered from severe bilateral polysegmentary pneumonia with a II-III degree of respiratory failure, chronic alcoholism, chronic hepatitis, secondary immunodeficiency. The patient started receiving MAXINIM (cephalosporin of the IV generation) in a dose of 1.0 gram intramuscularly every 12 hours. At the $3^{rd}$ day of the treatment the patient's condition ameliorated, dyspnea and cough subsided, and the body temperature went down. However, the paint started complaining of nausea, his functional liver tests showed elevated values of ALT and AST. The treatment protocol was completed with a C50 dilution of potentiated antibodies to MAXINIM in a dose of 1 tablet 3 times a day. The patient's condition kept improving, the nausea disappeared, and the ALT and AST values dropped to the upper bound of normal.

F. Patient K., aged 46, was taking RULIDE for acute prostatitis in a dose of 150 mg twice a day. After three days of the treatment the symptoms of prostatitis subsided but the patient started complaining of dizziness and distorted smell and taste of food. The treatment with a C30 dilution of potentiated antibodies to RULIDE in a dose of 1 tablet 3 times a day was started and within three days the taste and odor perception was back to normal and dizziness disappeared.

G. Patient G., aged 25, suffered from the exacerbation of chronic adnexitis after criminal abortion, polynarcomania, and secondary immunodeficiency. She was treated with CIPROBAY (125 mg 2 times a day). After 6 days of the treatment the patient felt better; however, she started having fainting spells and hot flashes. A C200 dilution of potentiated antibodies to CIPROBAY in a dose of 1 tablet twice a day was prescribed. Within the days the patient's complaints disappeared, her condition became satisfactory.

H. Patient Sh., aged 44, had been treated with CIPROFLOXACIN for the exacerbation of chronic suppurative obstructive bronchitis. The choice of the drug had been based on the results provided by the antibioticogram; the repeated use if this medication had been giving clinical success. However, in this case no positive bronchological dynamics was achieved after 2 weeks of treatment. The antibiotic was discontinued and the treatment with a C6 dilution of potentiated monoclonal antibodies to CIPROFLOXACIN in a dose of 1 tablet twice a day began. Within ten days all symptoms of bronchial obstruction disappeared, no suppurative mucus was seen during bronchoscopy. A conclusion was drawn on the anti-bacterial and anti-inflammatory effects of potentiated antibodies.

I. Patient I., aged 42, was staying in a phthisiologic hospital with an established diagnosis of infiltrative tuberculosis of the upper lobe of the right lung in the phase of disintegration and dissemination, with bacterioexcretion. After three months of the treatment with isoniazid, rifampicin, and streptomycin positive clinical and X-ray dynamics was achieved. However, the subsequent two months of the treatment with the antibacterial drugs did not bring any significant improvement of the patient's condition: infiltration and a cavern in the upper lobe of the right lung persisted and showed no tendency for a further reduction; the release of bacteria persisted as well. The in vitro resistance to antibiotics was not found at the initial stage of examinations or five months later. The treatment with a C200 dilution of potentiated antibodies to ISONIAZID, RIFAMPICIN, and STREPTOMYCIN in a dose of 1 tablet of each preparation daily made it possible to achieve positive X-ray dynamics within two months; the release of bacteria stopped.

J. Patient Ch., aged 36, was staying at the infectious hospital for amebic dysentery. After four days of the administration of ORNIDAZOLE (1.0 g per diem) the patient started complaining of somnolence and dizziness. The additional treatment with a C12 dilution of potentiated antibodies to ORNIDAZOLE in a dose of 1 tablet twice a day resulted in the elimination of the undesirable effects within subsequent four days.

EXAMPLE 41

Potentiated Antibodies to Chelating Agents

A. Patient D., aged 44, was undergoing a course of treatment with DOXORUBICIN (75 mg administrated intravenously once in 3 weeks) at the in-patient unit of an oncological dispensary for III degree breast cancer. For the prevention of myocardiopathy the patient was receiving CARDIOXANE intravenously 30 minutes before the injection of the cytostatic drug. The patient tolerated DOXORUBICIN well enough with a background treatment with CARDIOXANE; however, her hemoglobin level dropped to 70 g/l. It was suggested to include the administration of a C30 dilution of potentiated antibodies to CARDIOXANE in a dose of 1 tablet twice a day in the treatment protocol. Within subsequent three months the remission of the main disease was achieved and maintained; no signs of cardiac failure were observed and the hemoglobin level was 95-100 g/l.

EXAMPLE 42

Potentiated Antibodies to Anti-Gout Drugs

A. Patient Kh., aged 49, with the diagnosis of hypertensive disease and chronic gout had been taking 1.5 g of PROBENECIDE daily for the prevention of gout exacerbation caused by a diuretic (hypothiazide) he was receiving for his hypertension. The patient complained of nausea, weakness and painful sensation in his gums. The treatment with a C12 dilution of potentiated antibodies to PROBENECIDE in a dose of 1 tablet twice a day was started and three days later the patient started feeling better. The treatment with hypothiazide and PROBENECIDE was continued; the PROBENECIDE dose was reduced by 50% with no negative effect on the therapeutic action.

B. Patient V., aged 51, had been taking (on his physician's advice) IMODIUM (LOPERAMIDE) for chronic-diarrhea caused not by infection (presumably by heavy metal salts). The patient stated that the overall effect of the drug was positive but complained of dizziness. The treatment with a C50 dilution of potentiated antibodies to the piperidine group of IMODIUM in a dose of 1 tablet twice a day was started and after five days of the therapy with antibodies the unpleasant sensations ceased (with a persisting therapeutic effect of the drug).

EXAMPLE 43

Potentiated Antibodies to Autologous Antigens

Potentiated antibodies to DNA antigens.

Patient P., aged 24, with clinical diagnosis of systemic lupus erythematosus accompanied by kidney affection (nephrotic type glomerulonephritis) and heart injury (myocarditis), subacute course, III degree of activity had been taking prednisolone (50 mg daily) and curantyl (200 mg daily). Because of the lessening of the effect of prednisolone she was began to receive potentiated polyclonal antibodies to native DNA isolated from lymphocytes of the patient's peripheral blood. Antibodies were obtained by immunization of a rabbit with subsequent purification of the antiserum and its potentiation based on homeopathic technology. The intake of a C1000 dilution of potentiated antibodies to autoantigens of DNA in a dose of 1 tablet twice a day resulted in a marked inhibition of the activity of the autoimmune process within two weeks. The laboratory findings were as follows: ESR decreased from 50 to 16 mm/h, the titer of the antinuclear factor lowered. Catamnesis: 6 months of the intake of potentiated antibodies gave clinical and laboratory remission.

EXAMPLE 44

Potentiated Antibodies to Rhesus (Rh) Factor

Patient S., aged 28, $Rh^-$ (her husband was $Rh^+$) was admitted to hospital with the diagnosis of an 8-weeks pregnancy. This was her fourth pregnancy. She had a history of normal first pregnancy ending with normal delivery, the second pregnancy was interrupted by medical abortion at the term of 10 weeks, and the third pregnancy ended with antenatal death of the fetus because of the Rh conflict at the term of 38 weeks. In order to prevent the Rh conflict and to maintain the current pregnancy she started to take a C200 dilution of polyclonal potentiated antibodies to Rh factor beginning with the $8^{th}$ week in a dose of 1 tablet twice a week. Catamnesis: the therapy favored uncomplicated pregnancy, which ended with labor at term. The baby ($Rh^+$) was healthy without symptoms of hemolytic disease.

EXAMPLE 45

Potentiated Antibodies to Substances Causing Intoxication and/or Dependence

Potentiated antibodies to opiates.

A. Patient S., aged 28, had an almost uninterrupted 5-year history of intravenous self-injections of crude homemade acetylated opium (sultyga). He was admitted to a narcological unit 24 hours after the last injection. The patient was irritated and gloomy and complained of intense pains in his extremities, chills, and insomnia. The oral intake of 10 drops of a C200 dilution of a potentiated aqueous solution of natural antibodies to MORPHINE HYDROCHLORIDE every 15-30 minutes was prescribed. The antibodies had been isolated by affinity chromatography from the serum of a patient with chronic morphine dependency. The therapy resulted in a quick disappearance of vegetative disorders and the lessening of the intensity of the myalgia. Six hours after the beginning of the therapy the patient went to sleep. Two days later the withdrawal symptoms virtually disappeared. A conclusion was drawn on the sufficiency of monotherapy with antibodies to morphine in the case of the opiate withdrawal syndrome.

B. Patient K., aged 21, was admitted to a narcology unit with typical manifestations of the opiate withdrawal syndrome. Questioning revealed that she had been abusing crude homemade extract of poppy seed straw (koknar) in the form of intravenous self-injections in the course of two years. A combined therapy with a C1000 dilution of potentiated monoclonal antibodies to MORPHINE in a dose of 1 tablet once in 2 hours and a C200 dilution of potentiated antibodies to codeine in a dose of 1 tablet in the morning and 1 at bedtime was prescribed. Within 48 hours all manifestations of the withdrawal syndrome were completely arrested.

C. Patient I., aged 42, was emergently admitted to a narcology unit with the diagnosis of codeine overdosage. The patient was somnolent and had periodic bouts of nausea. The examination revealed depressed reflexes, bradycardia, and moderate hypotension. The patient was put on a slow intravenous infusion of 200 ml of an isotonic solution containing polyclonal potentiated antibodies to opiates of the phenotrene group mixed in the following proportions: 1 ml of a C200 dilution of antibodies to MORPHINE; 1 ml of a C1000 dilution to CODEINE; 1 ml of a C50 dilution to THEBAINE; 1 ml of a C3.0 dilution to PSEUDOMORPHINE; 1 ml of a C12 dilution of antibodies to NEOPINE. Within two hours after the beginning of the treatment the symptoms of intoxication completely disappeared.

D. Patient D., aged 16, had been inhaling heroin at least three times a week in the course of the last 1.5 months. On his parents' accord he was hospitalized in a restricted admission unit for 24 days. Two days after admission he became irritable, developed sleeping disorders, and complained of attraction to the drug when talking to his physician. The prescription was: a C1000 dilution of potentiated polyclonal antibodies to HEROIN in a dose of 1 tablet 6 times a day. Three weeks later the patient reported even mood and satisfactory sleep and appetite. During individual talks with a psychologist he denied having attraction to the drug. It was recommended to keep taking antibodies to heroin in a dose of 1 tablet a day. Two months after his discharge from hospital he (according to his mother's information) has never been noticed taking drugs.

E. Patient Kh., aged 24, had been injecting intravenously some crude homemade heroin preparations for three years. He was admitted to a narcology unit in a state of sopor. In view of the inefficiency of potentiated antibodies to heroin during his previous treatment, it was recommended to start the oral administration of a mixture of aqueous solutions of monoclonal antibodies to the following synthetic and semisynthetic opiates: a C50 dilution of antibodies to DIONINE (ethylmorphine); a C1000 dilution to PROMEDOL: a C30 dilution to PHENTANYL. Thirty minutes later the patient became fully conscious and oriented in time. His reflexes were moderately depressed. He told the physicians that he had self-injected a dose of an unknown drug at the discotheque.

Potentiated antibodies to barbiturates and other soporific drugs.

F. Patient B., aged 32, was admitted to an intensive care unit in the status epilepticus. According to his relatives, he had been taking various drugs of the barbiturate group both orally and intravenously in the course of the last years. The intravenous infusion of the following mixture of potentiated monoclonal antibodies to barbiturates was prescribed: a C50 dilution of antibodies to BARBAMYL (amytal sodium); a C200 dilution to NEMBUTAL (ethaminal sodium); a C1000 dilution to FANODORM (cyclobarbital) in a dose of 1 ml each. Within 15 minutes after the beginning of the therapy the status epilepticus was controlled, the patient lapsed into a stunned condition. During further observation at the hospital the patient was irritated and suffered from insomnia and dysphoria from time to time. He tried to get hold of soporific drugs. An interview revealed that he had also been taking drugs of the ureide group (bromural) and noxyron besides barbiturates. In view of this the patient was advised to take a C50 dilution of potentiated monoclonal antibodies to BROMURAL in combination with a C200 dilution of potentiated polyclonal antibodies to NOXYRON 1 tablet alternately every two hours. The patient's condition seriously improved: there was no dysphoria, he became less torpid, and his sleep was back to normal. He stopped searching for soporific drugs and was discharged in a satisfactory condition.

Potentiated antibodies to cannabinoids.

G. Patient S., aged 24, was admitted to a psychiatric unit with pronounced depressive disorders. He had had a long history of hashish use (up to 5-8 joints a day). As the treatment with antidepressants proved inefficient, the oral intake of 10 ml of an aqueous solution containing the following mixture of potentiated polyclonal antibodies to CANNABINOIDS: a C50 dilution of antibodies to canabidiol; a C30 dilution to cannabinol; a C200 dilution to (−)-trans-$\Delta^9$-tetrahydrocannabinol. After 10 days of the treatment the patient's mood became even and his sleep was back to normal. Two weeks after the beginning of the treatment with anti-bodies the patient was discharged in a satisfactory condition.

H. Patient D., aged 14, had been using drugs for 6 months. She used to chew the so-called bang (hashish tar). She was willing to be treated and his district narcologist prescribed potentiated monoclonal antibodies to CANNABINOIDS in a dose of 1 tablet every morning according to the following scheme: a C50 dilution of potentiated monoclonal antibodies to $\Delta^8$-tetrahydrocannabinol during the first two weeks of the month and potentiated monoclonal antibodies to $\Delta^9$-tetrahydrocannabinolic acid during the last two weeks. Six months of medical observation showed that the patient had given up drug abuse. The patient is socially adapted and continues her studies.

Potentiated antibodies to cocaine and its metabolites.

I. Patient S., aged 28, had been using crack (a mixture of cocaine with baking soda) for 1.5 years. He was admitted to a therapeutic unit with the diagnosis of cachexy caused by chronic hepatitis of an unknown origin. Two weeks of health-improving therapy and hepatotropic treatment did not produce any significant effect. In order to control asthenic symptoms the treatment was supplemented with tablets of a C50 dilution of monoclonal potentiated antibodies to COCAINE (in a dose of 1 tablet twice a day). After three weeks of the treatment the preparation was substituted by tablets containing polyclonal antibodies to cocaine metabolites: a C50 dilution of antibodies to benzoylecgonine and a C200 dilution of antibodies to ecgonine. The treatment resulted in the normalization of the patient's mood and sleep; he gained 18 kg of weight. Two months after the beginning of the therapy the patient was discharged in a satisfactory condition.

J. Patient O., aged 17, was brought to the narcological restricted admission unit by her parents. In the course of the last two months she had been self-injecting cocaine solutions intravenously. An interview with a psychologist revealed signs of a psychic dependence on this drug. The prescription was: a C50 dilution of polyclonal antibodies to a cocaine metabolite, NORCOCAINE, in a dose of 1 tablet 3 times a day during the first 10 days of hospital stay. The same pattern was applied to her second 10 days of hospital stay (a C200 dilution of polyclonal antibodies to METHYLECGONINE) and to the third 10-days' period (a C1000 dilution of polyclonal antibodies to HYDROXYCOCAINE) in the third decade of her hospital stay. The treatment with homeopathic doses of antibodies to cocaine metabolites resulted in a considerable improvement of the patient's condition of health: her mood became even and her sleep was back to normal. A test before discharge one month later revealed no signs of psychic dependence. Catamnesis four months later: the patient is socially adapted and has not been noticed using drugs.

Potentiated antibodies to benzodiazepines.

K. Patient S. aged 38, had a 20-year long history of the abuse of tranquilizers and psychotropic drugs of the benzodiazepine group. Against the background of the drug abuse the patient developed a psychoorganic syndrome with predominant astheno-apathic symptoms and the patient was granted the $2^{nd}$ degree of disability. The scheme of nootropic treatment prescribed by the district physician involved a long-term intake of polyclonal potentiated antibodies to a number of benzodiazepines, namely, a C50 dilution of antibodies to CHLOZEPID; a C50 dilution to diazepam; a C200 dilution to OXAZEPAM; a-C200 dilution to NITRAZEPAM; a C1000 dilution to LORAZEPAM. As a result a C1000 dilution of polyclonal potentiated antibodies to CLONAZEPAM proved to be the best choice for the patient. He had been taking them every day in a dose of 1 tablet twice a day for 14 months, which resulted in the improvement of his intellectual capacities and memory. Now his behavior is well ordered; the patient is capable of taking care of himself; his mother reports that he hasn't been using any sedatives during this period.

Potentiated antibodies to phenylalkylamines and other stimulants.

L. Patient C., aged 26, was admitted to a psychiatry department with the diagnosis of psychosis caused by ephedron abuse. Among the symptoms anxiety, alertness, alarming expectations, and paranoid attitude prevailed. The intravenous administration of a C50 dilution of potentiated monoclonal antibodies to EPHEDRON in a dose of 1 ml twice within the first hour of treatment was prescribed. After 1.5 hours of the therapy psychotic disorders disappeared. The patient's attitude to his delusional episode is critical.

M. Patient Kh., aged 41, engaged at diplomatic service was admitted to a intensive care unit because of a long period (about 18 hours) of somnolence. According to his wife's information, the patient used to indulge alone in an intravenous administration of some stimulants but definitely not cocaine. The prescription was: a slow intravenous infusion of physiological saline solution containing 1 ml of a C50 dilution of potentiated antibodies to AMPHETAMINE and 1 ml a C30 dilution of polyclonal potentiated antibodies to METH-AMPHETAMINE. Within fifteen minutes the lethargic symptoms were arrested. The patient was fully conscious and well oriented. He told the physician that he had administered a single dose of amphetamine intravenously.

N. Patient T., aged 17, administered himself ephedrine intravenously three times in the course of the last month for the first time in his life. On his own initiative he went to seek for narcologist's advice, as he was afraid of becoming an addict. The prescription was: the intake of a combined preparation containing polyclonal antibodies to EPHEDRINE and polyclonal antibodies to NOREPHEDRINE in a potentiated form (dilutions C50 and C200, respectively) in a dose of 1 tablet twice a day. For half a year the patient paid regular visits to his physician twice a month and reported no episodes of ephedrine use during this period.

O. Patient L., aged 25, sought for narcologist's advice on his own initiative. After 1.5 years of imprisonment he had become addicted to chifir (an extra strong tea brew) and used it at least 1-2-times a day. C50 dilution of potentiated polyclonal antibodies to CAFFEINE (1,3,7-trimethylxanthine) in a dose of 1 tablet twice a day. During his subsequent visits the patient stated that he had been drinking chifir very rarely (not more often than once a week) but could not give it up altogether.

Potentiated antibodies to hallucinogens (psychedelic drugs).

P. Patient K., aged 28, was brought to the psychiatric department from a hotel where he had attracted the hotel staffs attention by his inadequate behavior: he was contemplating something, used to freeze suddenly and stand motionless; he was poorly oriented in the situation around him. In response to physician's questions the patient answered that he used to take pieces of blotting paper impregnated with LSD, sublingually. A single dose (1 ml) of a C200 dilution of a solution containing potentiated polyclonal antibodies to lysergic acid diethylamide (LSD) was administered. Fifteen minutes after the administration of the preparation the psychotic disorders were arrested.

Q. Two A. brothers, aged 16 and 19, with the diagnosis of poisoning with dried ink fungi were admitted to a psychiatric unit. As the quantity of potentiated preparation available at that moment at the unit was insufficient, one of the patients received intravenously 1 ml of a C200 dilution of potentiated polyclonal antibodies to PSILOCIN and the other, 1 ml of a C50 dilution of potentiated polyclonal antibodies to PSILOCYBIN. Within an hour the condition of both patients returned to normal, their excitement and unrestraint disappeared, and they both went to sleep. A conclusion was drawn on high efficiency of both preparations.

R. Patient D., aged 19, was admitted to a neurology unit for manifestations of catalepsia. In view of the fact that the patient had been taking the drug phenycyclidine (PCP), she underwent hourly intramuscular administrations of 1 ml of a D3 dilution of the solution of potentiated antibodies to PHENYCYCLIDINE. Within three hours the cataleptic syndrome was completely arrested.

S. Patient A., aged 38, has the $2^{nd}$ degree of disability because of paranoid schizophrenia. For fifteen years he had been taking high daily doses of haloperidol in combination with parcopan or cyclodol for the prevention of narcolepsia and had already developed physical dependence on them. The attending physician started reducing gradually the dose of cyclodol ending up with replacing it completely with a C30 dilution of potentiated polyclonal antibodies to CYCLODOL in a dose of 1 tablet in the morning and 1 tablet at bedtime every day. The patient keeps taking haloperidol and doesn't have any neuroleptic symptoms; no requests for cyclodol prescription.

Potentiated antibodies to alkaloids of tobacco.

T. Patient I., aged 29, consulted a narcologist for tobacco smoking. Because the neuropharmacological preparations he used to take earlier had not succeeded to rid him of the bad habit, the physician prescribed a C200 dilution of a potentiated antiserum to NICOTINE in a dose of 1 tablet 3 times a day. Catamnesis 3 months later was as follows: in the course of the first weeks of the therapy with antibodies the patient's craving for tobacco was enhanced and he smoked more often. Later on, the situation changed, his craving receded, he was able to gradually reduce the number of smoked cigarettes and finally to give up smoking altogether.

Potentiated antibodies to alcohol.

U. Patient B., aged 35, was admitted to a narcological hospital with pronounced symptoms of alcohol withdrawal. A C200 dilution of potentiated monoclonal antibodies to ETHANOL in a dose of 1 sublingual tablet every 15 minutes was prescribed. Within two hours of the therapy the patient's condition significantly improved: the tremor, hyperhydrosis, and weakness disappeared, the patient went to sleep. Twenty-four hours later he was discharged. Conclusion: potentiated antibodies to ethanol have a therapeutic effect in the case of the alcohol withdrawal syndrome.

EXAMPLE 46

Potentiated Antibodies to Antigens of Fetal and Primordial Tissues and Tissue Cultures A. Patient A. was a newborn baby 27 days old. He was born with symptoms of perinatal encephalopathy. As immunoenzyme diagnostic methods had revealed elevated levels of embryotropic neurospecific antigens in mother before this pregnancy, it was decided to administer to the baby a C200 dilution of a potentiated polyclonal antiserum to bovine fetal brain-specific non-species-specific protein (antigen), 14-3-2 (brain-specific enolase), in an oral dose of 5 drops of an aqueous solution to be administered 3 times a day. In the course of the treatment neurological symptoms subsided gradually; the reflexes of oral and spinal automatism restored and muscle hypertonus receded. The baby became calmer and started active breast sucking. A conclusion was drawn on the efficiency of potentiated antibodies to the said fetal antigen controlling normal morphogenesis of the central nervous system in the treatment of perinatal encephalopathy.

B. Patient D., aged 4, with an established diagnosis of mental retardation had been receiving a C1000 dilution of monoclonal potentiated antibodies to PRIMORDIAL ANTIGEN NESTIN, a protein marker of neuron stem cells, in a dose of 5 drops of an aqueous solution once a day in the morning for six months with the purpose of enhancing the child's intellectual capacities. After six months of the treatment a neuropsychological examination showed that D' s intellect and memory were up to the standard age level; the child's kindergarten tutor reported that the boy comprehended and learned the material well in class.

C. Patient I., aged 8, with an established diagnosis of Down's syndrome had been receiving a C200 dilution of potentiated polyclonal antibodies to A-FETOPROTEIN to be taken in a dose of 1 tablet a day for the first 12 months and in a dose of 1 tablet once in 3 days for subsequent 6 months. The neuropsychological examination by Bailey's method revealed a marked enhancement of the patient's intellect 1.5 years later. The patient's behavior is well ordered; he is adapted to being with other children.

D. Patient S., aged 18, suffered from myasthenia of an unknown origin. In view of the inefficiency of conventional drugs the treatment was supplemented by the oral intake of a C30 dilution of potentiated polyclonal antibodies to the culture of neuronal stem cell of the tera-1 line enriched with the protein extract of the embryonic tissue in a dose of 1 ml 3 times a day for 6 months. The combined treatment resulted in an increased tolerance of physical strain, receded bulbar symptoms, diplopia, and ptosis, which made it possible to reduce the daily doses of corticosteroid drugs several times.

E. Patient M., aged 42, suffered from the astheno-neurological syndrome accompanying the remote period of vernal encephalitis. As conventional therapy proved its inefficiency, it was decided to prescribe the oral intake of a C200 dilution of potentiated polyclonal antibodies to EMBRYONIC NEOCORTEX (the antiserum was obtained by immunization of rabbits with tissues from the occipital zone of the brain cortex of 15-day old embryos of Wistar line rats) in a dose of 1 ml twice a day, for 6 months. In the course of treatment the patient's asthenic symptoms became less pronounced, his ability to work was restored, though disseminated microsymptoms persisted in his neurological status.

F. Patient K., aged 39, suffered from chronic alcoholism, grade II. He went to seek for narcologist's advice declaring his desire to start a sober life and asking for a new method of treatment because those he had already tried were of little effect. The prescription was: a regular intake of a C1000 dilution of polyclonal potentiated antibodies to homogenized hippocampi of embryos of Wistar line rats (hippocampi of several dozens of syngenic fetuses were used for immunization) in a dose of 1 tablet once a day. The remission had been lasting for 8 months, in the course of this period of medical observation no episodes of consuming alcoholic beverages have been registered, the patient states the absence of craving for alcohol.

G. Patient A., aged 8, suffered from liver cirrhosis of an unknown etiology. As the conventional therapy had no significant effect, the oral intake of a C4 dilution of polyclonal potentiated antibodies to homogenized liver of the human fetus was prescribed in a dose of 1 ml 3 times a day. During four months of the therapy a clinical improvement of the patient's condition was observed, manifestations of general intoxication symptoms and liver failure subsided. The patient's emotional tone rose, the paleness of skin, the icteric hue of the scleras, and spider-like hemangiomas disappeared; the size of the liver diminished. A conclusion was drawn on high efficiency of this mode of treatment.

EXAMPLE 47

Potentiated Antibodies to Tissues or Tissue Cultures

A. Patient O., aged 8, suffers from a malignant course of insulin-dependent diabetes mellitus. The intranasal administration of a C50 dilution of potentiated polyclonal antibodies to a culture of insular cells of the pancreas of newborn rabbits in a dose of 1 ml 3 times a day was prescribed with therapeutic purposes. After three months of the therapy the course of illness became stable, the blood glucose level went down, and the disposition to ketoacidosis receded. There were no comas or hypoglycemic episodes during the period of the treatment and the amount of insulin intake was reduced by 50%.

B. Patient P., aged 35, suffered from insulin-dependent diabetes mellitus (mild course). As the patient was unwilling to take insulin, the recommendation was to start the oral intake of 1 ml of a C50 dilution of an aqueous solution of polyclonal potentiated antiserum to insular cells of the pancreas of a newborn calf once a day. As a result of the monotherapy with this preparation, the patient was feeling well. Her blood glucose level was within normal limits. The patient did not take insulin any more.

C. Patient V. aged 56, suffered from obstructing atherosclerosis of coronary arteries and angina decubitus. In view of the inefficiency of conventional therapy the prescription was to take intranasally a C30 dilution of potentiated polyclonal antibodies to the homogenized heart of a newborn rabbit in a dose of 3 drops of an aqueous solution 5 times a day. After six months of the therapy the intensity of pain was reduced, the patient had pain much more seldom and only after a sufficiently strong physical strain; his blood lipid formula became normal and the dose of nitrate drugs was reduced approximately by 50%.

Thus, an analysis of the examples given above shows that the activated form of ultra-low doses of antibodies to an antigen (a substance or a pharmaceutical agent) does not produced the well-known immunological effect of binding the antigen and inhibiting its activity; on the contrary, it reproduced the antigen's activity in a modified form, which results in a partial or complete reduction of the pathological syndrome, in the regulation of whose mechanisms of development the said antigen is involved. In this case such antigen-associated side effects as toxicity, addiction, and tolerance are absent.

In addition, activated antibodies in ultra-low doses potentiate (reinforce) the effect of an antigen (a pharmaceutical agent) on their combined or simultaneous administration, which makes it possible to reduce the dose of the pharmaceutical agent and to minimize its side effects.

The administration of activated forms of ultra-low doses of antibodies to a substance or a pharmaceutical agent favors the reduction of the intensity of the pathological syndromes (acute or chronic intoxication, post-intoxication disorders, dependence) caused by this substance or pharmaceutical agent.

Experimental studies of activated forms of ultra-low doses of antibodies make it possible to determine their therapeutic properties even in situations where the biological activity of the initial antigen remains unknown.

The invention claimed is:

1. A method of treating a disorder or condition of viral etiology, said method comprising administering to a patient in need thereof a homeopathically potentized form of an antibody to an antigen, which antigen is gamma interferon.

2. The method of claim 1, wherein said antibody is selected from monoclonal, polyclonal and natural antibodies.

3. The method of claim 1, wherein said homeopathically potentized form of an antibody is produced by homeopathic potentization.

* * * * *